US012797100B2

(12) United States Patent
Ueda

(10) Patent No.: US 12,797,100 B2
(45) Date of Patent: Nov. 17, 2026

(54) ENDOSCOPE TREATMENT TOOL, ENDOSCOPE DEVICE, AND TREATMENT METHOD

(71) Applicant: FUJIFILM Corporation, Tokyo (JP)

(72) Inventor: Yoshihiro Ueda, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 403 days.

(21) Appl. No.: 18/317,930

(22) Filed: May 16, 2023

(65) Prior Publication Data

US 2023/0277204 A1 Sep. 7, 2023

Related U.S. Application Data

(63) Continuation of application No. PCT/JP2021/040180, filed on Oct. 29, 2021.

(Continued)

(51) Int. Cl.

| | |
|---|---|
| ***A61B 17/29*** | (2006.01) |
| ***A61B 1/018*** | (2006.01) |
| ***A61B 17/00*** | (2006.01) |

(52) U.S. Cl.

CPC .......... *A61B 17/2909* (2013.01); *A61B 1/018* (2013.01); *A61B 2017/00862* (2013.01);

(Continued)

(58) Field of Classification Search

CPC ................ A61B 17/2909; A61B 1/018; A61B 2017/00862; A61B 2017/2905;

(Continued)

(56) References Cited

U.S. PATENT DOCUMENTS 5,014,685 A * 5/1991 Takahashi ......... A61M 25/0136 600/148
8,906,013 B2 12/2014 Romoscanu (Continued)

FOREIGN PATENT DOCUMENTS

CN 103140158 6/2013
CN 111727017 9/2020

(Continued)

OTHER PUBLICATIONS

"International Search Report (Form PCT/ISA/210) of PCT/JP2021/040180," mailed on Jan. 11, 2022, with English translation thereof, pp. 1-5.

(Continued)

*Primary Examiner* — Brooke Labranche
*Assistant Examiner* — Rachael L Geiger
(74) *Attorney, Agent, or Firm* — JCIPRNET

(57) ABSTRACT

An endoscope treatment tool includes: a distal end part provided with an openable and closable grip part; a bendable part provided adjacent to the distal end part and being bendable; an operating part into which an operation of closing the grip part and an operation of bending the bendable part are input; and an operation wire that transmits the operations at the operating part respectively to the grip part and the bendable part, and the operating part includes an operating part body that movably holds a wire holding part to which the operation wire is connected, and an operation handle that moves the wire holding part, and has a friction adjusting mechanism that increases a frictional force locking the wire holding part to correspond to an increase in a pulled amount of the operation wire caused by the wire holding part interlocked with an operation of the operation handle.

15 Claims, 31 Drawing Sheets

Related U.S. Application Data

(60) Provisional application No. 63/118,974, filed on Nov. 30, 2020.

(52) U.S. Cl.
CPC ................. *A61B 2017/2905* (2013.01); *A61B 2017/2912* (2013.01); *A61B 2017/2948* (2013.01)

(58) Field of Classification Search
CPC .... A61B 2017/2912; A61B 2017/2948; A61B 2017/00269; A61B 2017/00292; A61B 2017/00314; A61B 2017/00318; A61B 2017/00424; A61B 2017/00438; A61B 2017/2919; A61B 17/29
See application file for complete search history.

(56) References Cited

U.S. PATENT DOCUMENTS

| | | | | |
|---|---|---|---|---|
| 8,911,362 | B2 | 12/2014 | Kaneko | |
| 2008/0294191 | A1* | 11/2008 | Lee | A61B 17/29 606/1 |
| 2015/0099928 | A1* | 4/2015 | Smith | A61M 5/178 514/777 |
| 2019/0059700 | A1 | 2/2019 | Matsuda | |
| 2020/0352422 | A1* | 11/2020 | Dejima | A61B 17/29 |
| 2024/0324863 | A1 | 10/2024 | Dejima et al. | |

FOREIGN PATENT DOCUMENTS

| | | |
|---|---|---|
| JP | 2011050643 | 3/2011 |
| JP | 2012100683 | 5/2012 |
| WO | 2019172318 | 9/2019 |

OTHER PUBLICATIONS

"Written Opinion of the International Searching Authority (Form PCT/ISA/237) of PCT/JP2021/040180," mailed on Jan. 11, 2022, with English translation thereof, pp. 1-6.
"Search Report of Europe Counterpart Application", issued on Apr. 11, 2024, pp. 1-8.
"Notice of Reasons for Refusal of Japan Counterpart Application", issued on Aug. 26, 2025, with English translation thereof, p. 1-p. 5.
"The First Office Action of China Counterpart Application", with English translation thereof, issued on Dec. 11, 2025, pp. 1-16.
"Office Action of China Counterpart Application", issued on Jun. 3, 2026, with English translation thereof, pp. 1-24.
"The Third Office Action of China Counterpart Application No. 202180079887.6", issued on Aug. 26, 2026, with English translation thereof, p. 1-p. 14.
"Office Action of Europe Counterpart Application No. 21897631.4", issued on Aug. 27, 2026, p. 1-p. 7.

* cited by examiner

ENDOSCOPE TREATMENT TOOL, ENDOSCOPE DEVICE, AND TREATMENT METHOD

CROSS REFERENCE TO RELATED APPLICATION

This is a continuation of International Application No. PCT/JP2021/040180 filed on Oct. 29, 2021, and claims priority from U.S. Provisional Application No. 63/118,974 filed on Nov. 30, 2020, the entire disclosure of which is incorporated herein by reference.

BACKGROUND OF THE INVENTION

1. Field of the Invention

The present invention relates to an endoscope treatment tool, an endoscope device, and a treatment method.

2. Description of the Related Art

In the related art, various types of treatment are performed on a living body by combining an endoscope device and an endoscope treatment tool. Endoscopic submucosal dissection (ESD) is known as an example of treatment. For example, an inner wall of the esophagus, stomach, large intestine, or the like to which ESD is applied consists of three layers including a mucous membrane layer, a submucosal layer, and a muscular layer. In ESD, a lesion part of the mucous membrane layer including the submucosal layer is peeled off, and it is also possible to collectively excise, for example, a relatively large lesion part which exceeds 2 cm.

As an example of the endoscope treatment tool, for example, WO2019/172318A discloses an endoscope treatment tool comprising an insertion portion that is insertable into a body, an operating part, and a single operation wire that extends from the operating part to the insertion portion and that is pulled to an operating part side in response to an operation of the operating part. The insertion portion includes a distal end part that has an openable closable grip part, a bendable part that is provided to be adjacent to the operating part side of the distal end part and that is bendable, and a connecting part that connects the bendable part and the operating part to each other. In the endoscope treatment tool, in response to the operation of the operating part, the connecting part is moved forward and backward along a longitudinal axis of the connecting part and is rotated about the longitudinal axis of the connecting part. As the connecting part is moved forward and backward or is rotated, the grip part moves forward and backward or rotates. As the operation wire is pulled, the grip part is closed, and the bendable part bends in a state where the grip part is closed.

SUMMARY OF THE INVENTION

In the endoscope treatment tool disclosed in WO2019/172318A, the bendable part is bent by a swingable operation handle that pulls the operation wire of the operating part. In this case, with an elastic force that causes the bent bendable part to be restored to a state before bending and an elastic force of a lesion part pulled up by the grip part, the pulled operation wire is pulled in an anti-pulling direction to be restored to a state before pulling. For this reason, at a part that moves relatively such as a portion of a swinging support shaft of the operation handle and a sliding portion of a slider which supports the operation wire, for example, a friction member made of rubber or the like is provided, and an operation state of the operation handle is maintained. In addition, also a configuration where a biasing member such as a spring is used and the operation handle is biased in a pulling direction is described in WO2019/172318A.

However, although the restoration force of the operation wire in the anti-pulling direction increases with an increase in the pulled amount, the retention power of the friction member or the biasing member is constant. For this reason, it is difficult to adjust the operating part. For example, in a case where the retention power is set to be adapted to the maximum value of the restoration force, an operation of the operation handle becomes heavy, and in a case where the retention power is small, the operation state of the operation handle cannot be maintained.

The present invention is devised in view of the circumstances described above and proposes an endoscope treatment tool, an endoscope device, and a treatment method that are excellent in the operability of an operating part which operates a distal end part.

According to an aspect of the present invention, there is provided an endoscope treatment tool comprising a distal end part that is provided with an openable and closable grip part, a bendable part that is provided to be adjacent to the distal end part and that is bendable, an operating part into which an operation of closing the grip part and an operation of bending the bendable part are input, and an operation wire that transmits the operations at the operating part respectively to the grip part and the bendable part, in which the operating part includes an operating part body that movably holds a wire holding part to which the operation wire is connected, and an operation handle that moves the wire holding part, and has a friction adjusting mechanism that increases a frictional force for locking the wire holding part to correspond to an increase in a pulled amount of the operation wire which is caused by the wire holding part interlocked with an operation of the operation handle.

According to another aspect of the present invention, there is provided an endoscope device comprising a first treatment tool that is the endoscope treatment tool, a second treatment tool, and an endoscope that has a first treatment tool channel into which the first treatment tool is insertable and a second treatment tool channel into which the second treatment tool is insertable.

According to still another aspect of the present invention, there is provided a treatment method comprising, by using the endoscope device, disposing the distal end part of the first treatment tool at a lesion part in a body through the first treatment tool channel of the endoscope, gripping the lesion part with the grip part of the first treatment tool, lifting, in a state where the lesion part is gripped, the lesion part by bending the bendable part of the first treatment tool, and treating, in a state where the lesion part is lifted, a lower part of the lesion part with the second treatment tool inserted into the second treatment tool channel of the endoscope.

With the present invention, the endoscope treatment tool, the endoscope device, and the treatment method that are excellent in the operability of the operating part which operates the distal end part can be provided.

DESCRIPTION OF THE PREFERRED EMBODIMENTS

Figure 1:
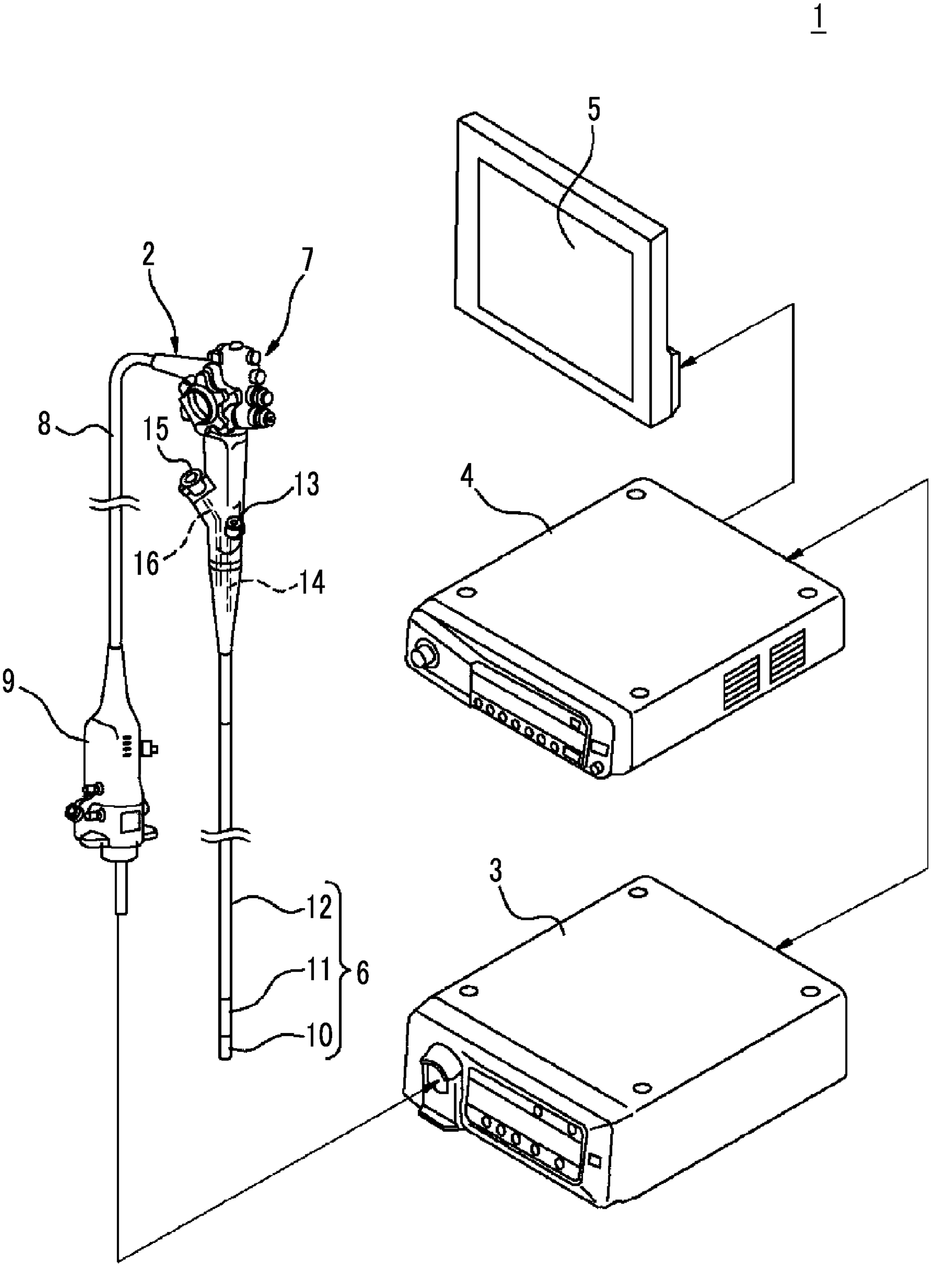
FIG. 1 is a view showing an example of an endoscope system, which is for describing an embodiment of the present invention.

Hereinafter, an endoscope treatment tool according to an embodiment of the present invention will be described with reference to FIGS. 1 to 25. FIG. 1 shows an example of an endoscope system for describing the embodiment of the present invention.

An endoscope system 1 comprises an endoscope 2, a light source device 3, and a processor 4. The endoscope 2 has an endoscope insertion part 6 that is inserted into a subject, an endoscope operating part 7 that is connected to the endoscope insertion part 6, and a universal cord 8 that extends from the endoscope operating part 7. The endoscope insertion part 6 is configured by an endoscope distal end part 10, an endoscope bendable part 11 that is connected to the endoscope distal end part 10, and an endoscope connecting part 12 that connects the endoscope bendable part 11 to the endoscope operating part 7.

An imaging apparatus including an imaging element is mounted on the endoscope distal end part 10. The endoscope bendable part 11 is configured to be bendable, and the bending of the endoscope bendable part 11 is operated by the endoscope operating part 7. In addition, the endoscope connecting part 12 is configured to be flexible so as to be deformable along a shape of an insertion passage in the subject.

The endoscope operating part 7 is provided with an operation button for operating image pick-up using the imaging apparatus and an operation knob for operating the bending of the endoscope bendable part 11. In addition, the endoscope operating part 7 is provided with a first treatment tool insertion opening 13 and a second treatment tool insertion opening 15, into which an endoscope treatment tool 20 (see FIG. 2) is insertable. Inside the endoscope insertion part 6, a first treatment tool channel 14 that reaches the endoscope distal end part 10 from the first treatment tool insertion opening 13 and that is open to an edge surface of the endoscope distal end part 10 and a second treatment tool channel 16 that reaches the endoscope distal end part 10 from the second treatment tool insertion opening 15 and that is open to the edge surface of the endoscope distal end part 10 are provided.

A light guide and a cable are provided inside the endoscope insertion part 6, the endoscope operating part 7, and the universal cord 8. A connector 9 is provided at a terminal of the universal cord 8. The endoscope 2 is connected to the light source device 3 and the processor 4 via the connector 9.

Illumination light generated by the light source device 3 is guided to the endoscope distal end part 10 via the light guide and is emitted from the endoscope distal end part 10. In addition, operating power of the imaging element, a control signal for driving the imaging element, and an image signal output from the imaging element are transmitted between the processor 4 and the imaging apparatus via the cable. The processor 4 processes the input image signal to generate image data of an observation site in the subject, displays the generated image data on a monitor 5, and records the generated image data.

Figure 2:
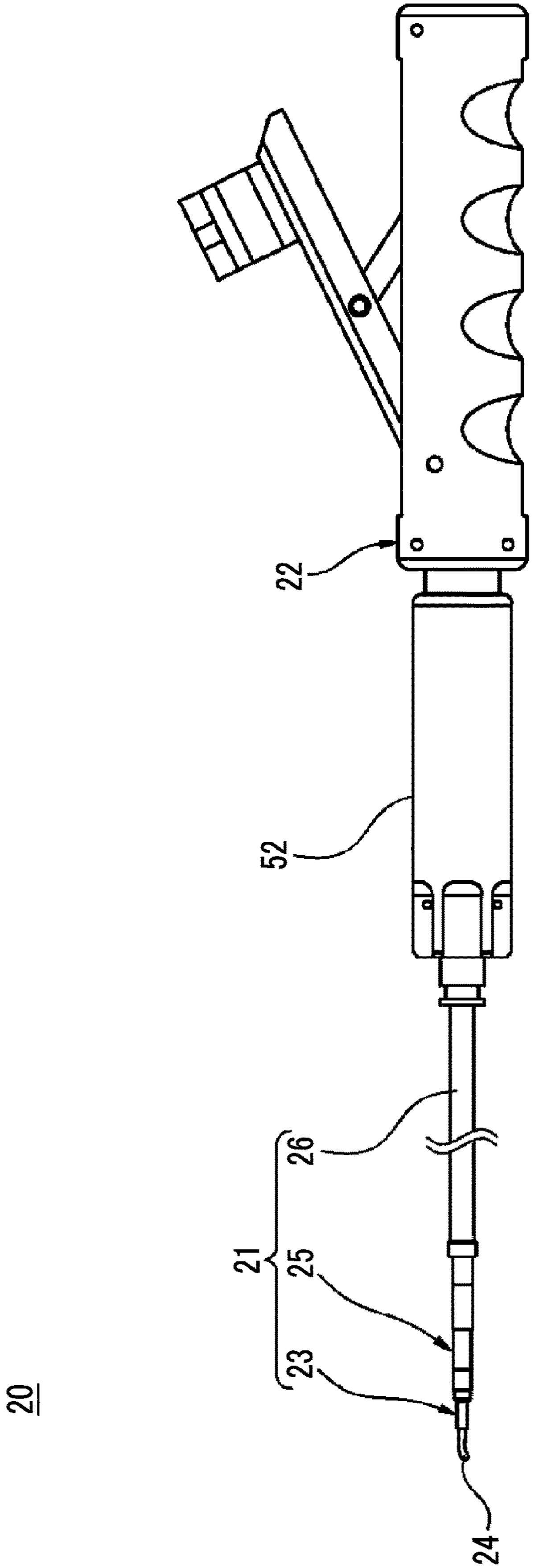
FIG. 2 is a view showing an example of an endoscope treatment tool, which is for describing the embodiment of the present invention.

FIG. 2 shows an example of the endoscope treatment tool 20, which is for describing the embodiment of the present invention.

The endoscope treatment tool 20 comprises an insertion part 21 that is insertable into the first treatment tool channel 14 (see FIG. 1), a treatment tool operating part 22 (hereinafter, simply referred to as the "operating part 22"), and a fixing unit 52 that is attached and fixed to the endoscope operating part 7. The insertion part 21 includes a distal end part 23 that has a grip part 24 operated to be opened and closed by the operating part 22, a bendable part 25 that is provided to be adjacent to an operating part side of the distal end part 23, and a connecting part 26 that connects the bendable part 25 and the operating part 22 to each other.

In a case where the insertion part 21 is inserted into the first treatment tool channel 14, the connecting part 26 is accommodated in the first treatment tool channel 14, and the distal end part 23 and the bendable part 25 protrude from the edge surface of the endoscope distal end part 10 (see FIG. 1). Similar to the endoscope connecting part 12, the connecting part 26 accommodated in the first treatment tool channel 14 is configured to be flexible so as to be deformable along the shape of the insertion passage in the subject. The connecting part 26 is an example of a soft portion of the present invention.

Figure 3:
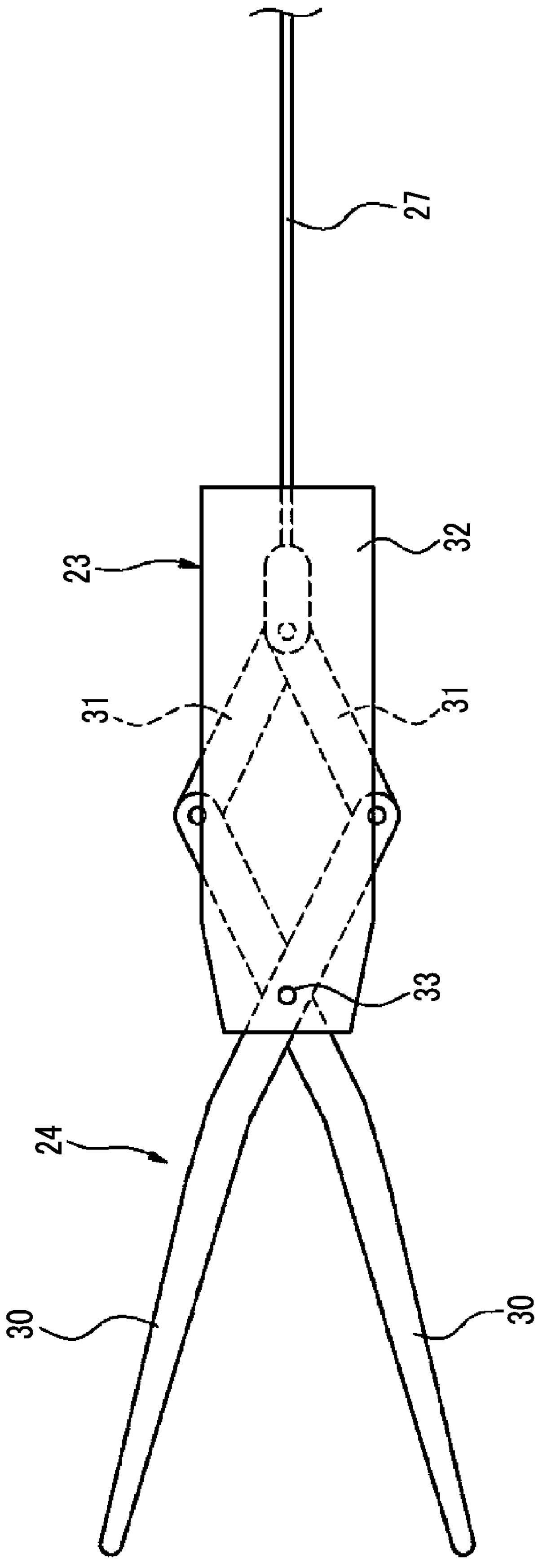
FIG. 3 is a view showing a configuration of a grip part of a distal end part of the endoscope treatment tool of FIG. 2.
Figure 4:
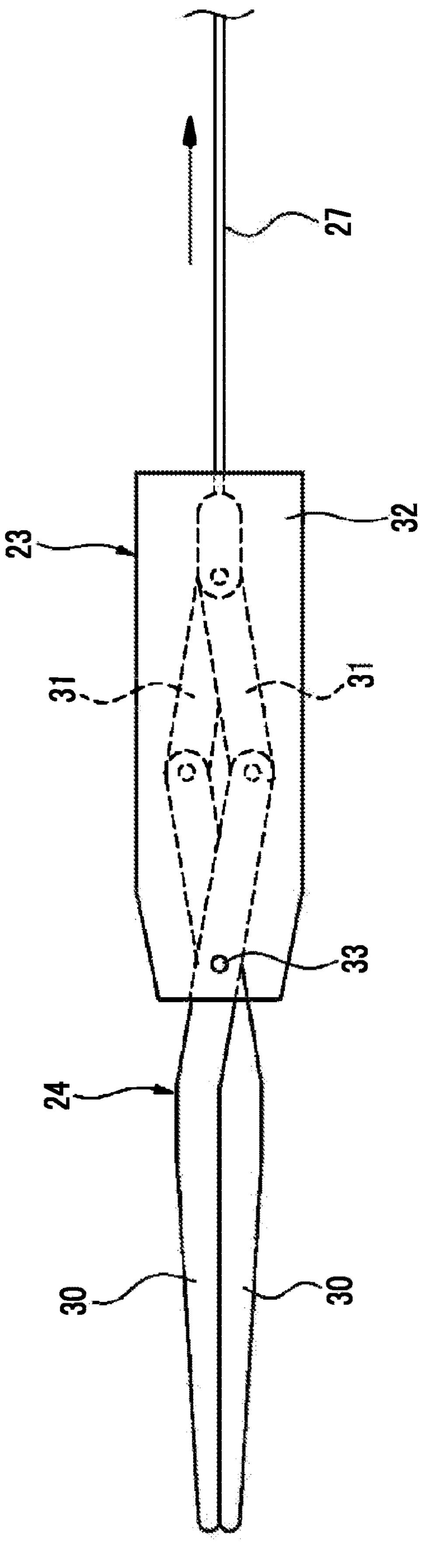
FIG. 4 is a view showing an operation of the grip part of FIG. 3.

FIGS. 3 and 4 show a configuration and an operation of the grip part 24 of the distal end part 23 in the endoscope treatment tool 20.

In the example shown in FIG. 3, the grip part 24 has a pair of grip claws 30 and a pair of link members 31. The distal end part 23 has a support 32 that supports the pair of grip claws 30 so as to be movable rotationally. The pair of grip claws 30 are disposed to intersect each other, and a pin 33 is provided to penetrate an intersecting portion of the pair of grip claws 30. The pin 33 is fixed to the support 32. The grip claws 30 are supported by the support 32 so as to be movable rotationally about the pin 33 which is a rotational movement shaft.

Distal end parts of the link members 31 are coupled to proximal end parts of the grip claws 30 so as to be movable rotationally, and an operation wire 27 is connected to proximal end parts of the link members 31. The operation wire 27 reaches the operating part 22 from the distal end part 23 via the bendable part 25 and the connecting part 26 and is pulled to an operating part 22 side or is pushed out to a distal end part 23 side in response to an operation of the operating part 22.

FIG. 3 shows a state where the operation wire 27 is pushed out to the distal end part 23 side, and distal end parts of the pair of grip claws 30 are open. As the operation wire 27 is pulled to the operating part 22 side, the distal end parts of the pair of grip claws 30 are closed as shown in FIG. 4. A part to be treated of a living body is gripped by the distal end parts of the pair of closed grip claws 30.

Figure 5:
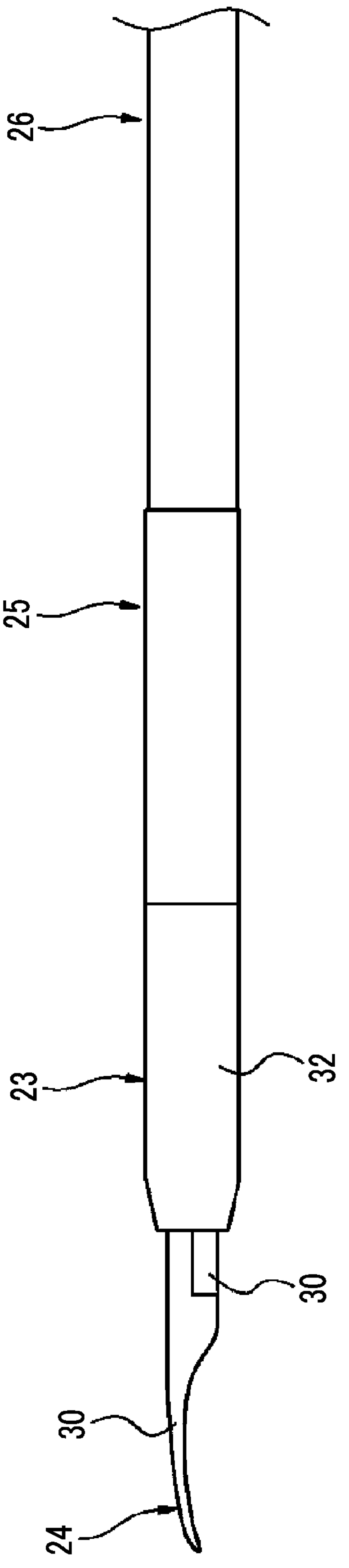
FIG. 5 is a view showing configurations of a bendable part and a connecting part of the endoscope treatment tool of FIG. 2.
Figure 6:
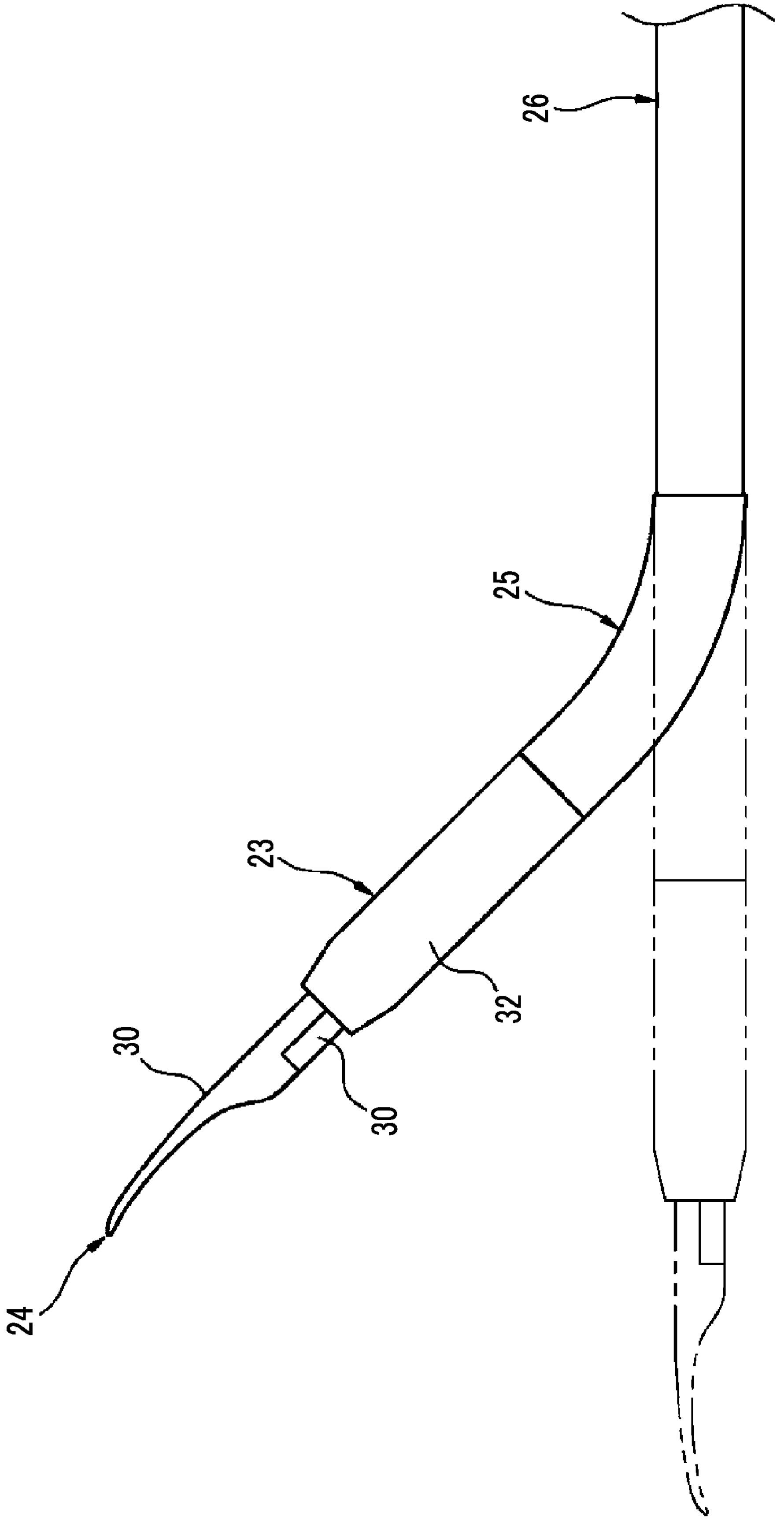
FIG. 6 is a view showing an operation of the bendable part of FIG. 5.

FIGS. 5 and 6 show configurations and operations of the bendable part 25 and the connecting part 26 in the endoscope treatment tool 20.

The connecting part 26 has flexibility and also has stiffness that allows translational and rotational power to be transmitted from the operating part 22 side to a bendable part 25 side. Such a connecting part 26 can be configured, for example, such that an outer periphery of a screw pipe, which is formed by spirally winding a strip plate material made of a metal, is covered with a mesh pipe formed by braiding a wire made of a metal and an outer periphery of the mesh pipe is covered with an outer coat made of a resin. As shown in FIG. 6, the bendable part 25 operated to be bent by the operating part 22 is bendable in a direction substantially perpendicular to a plane including an opening and closing direction of the pair of grip claws 30. In short, a bending operation plane including a bending operating direction of the bendable part 25 is in a direction substantially perpendicular to an opening and closing operation plane of the pair of grip claws 30.

Figure 7:
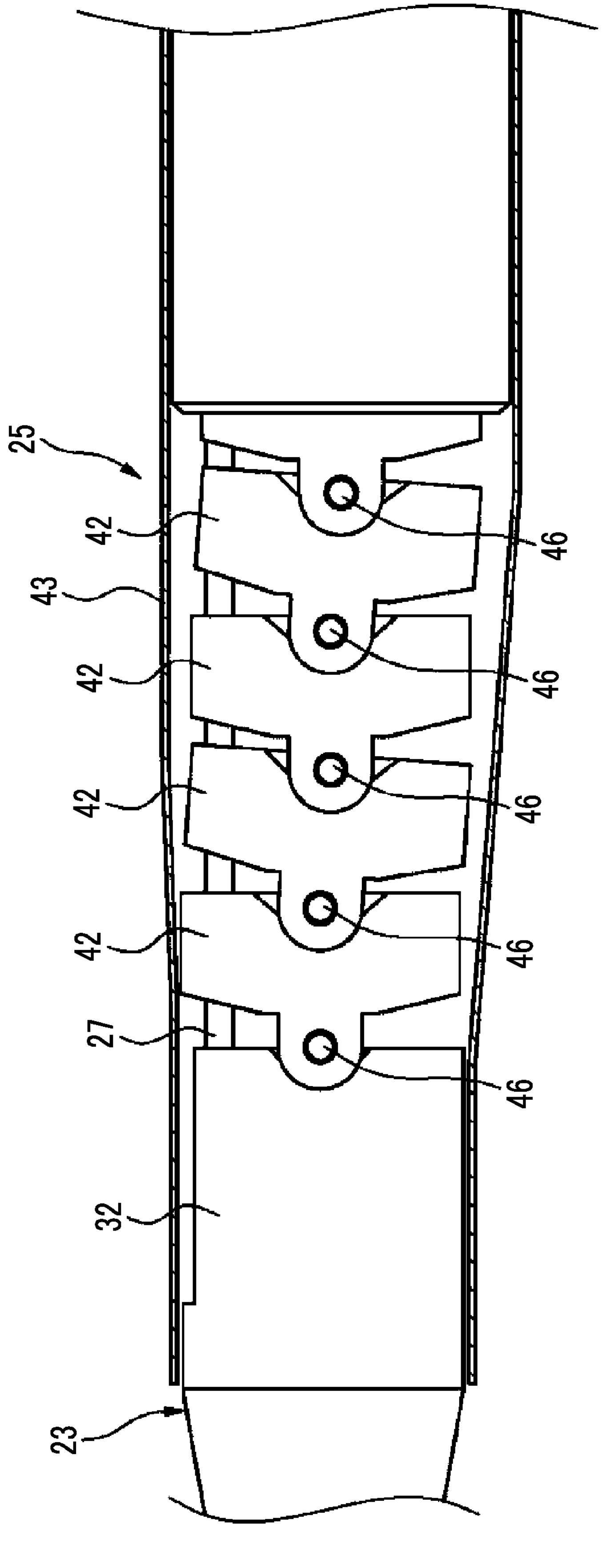
FIG. 7 is a view showing a configuration of an inside of the bendable part of FIG. 5.
Figure 8:
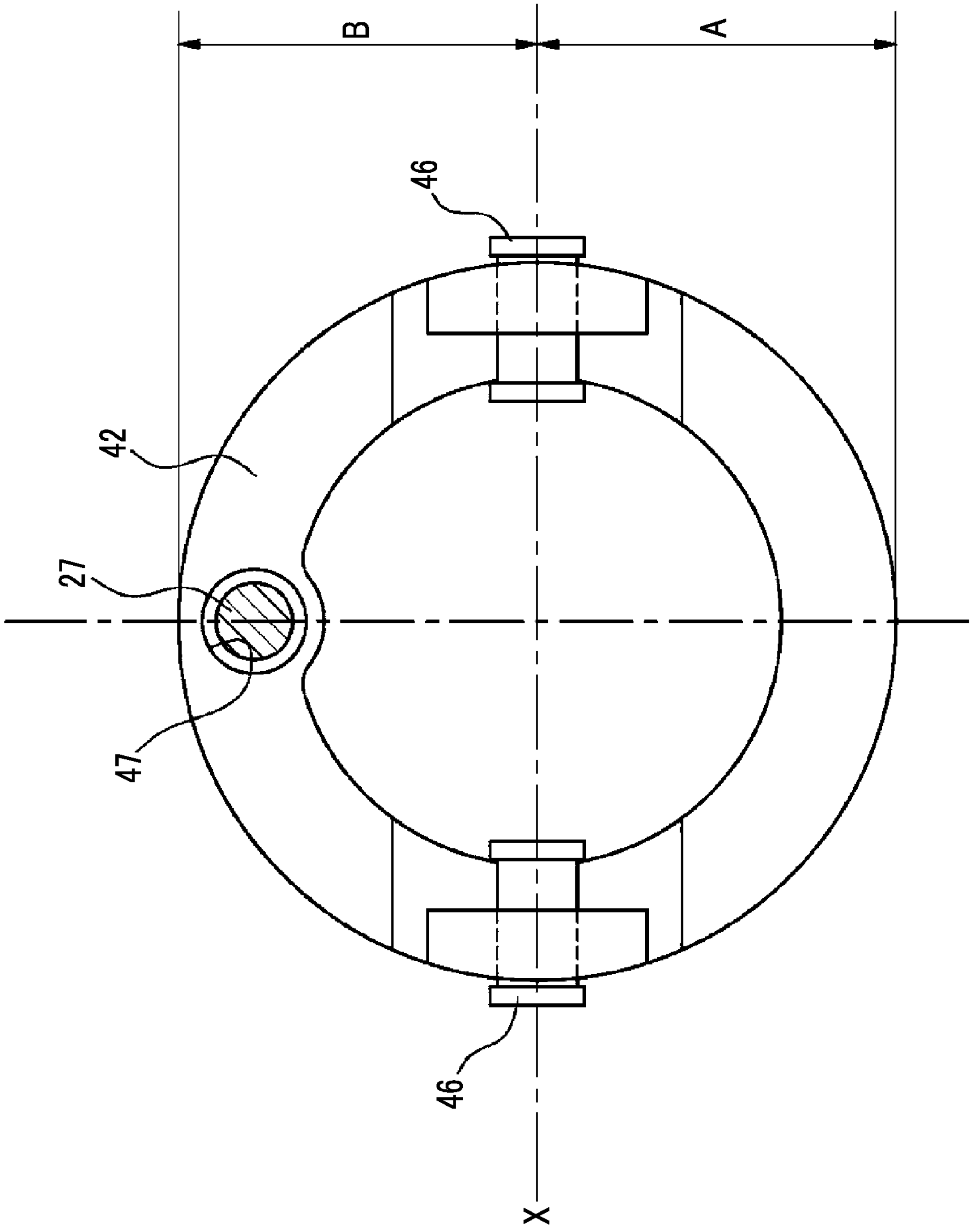
FIG. 8 is a view showing the configuration of the inside of the bendable part of FIG. 5.
Figure 9:
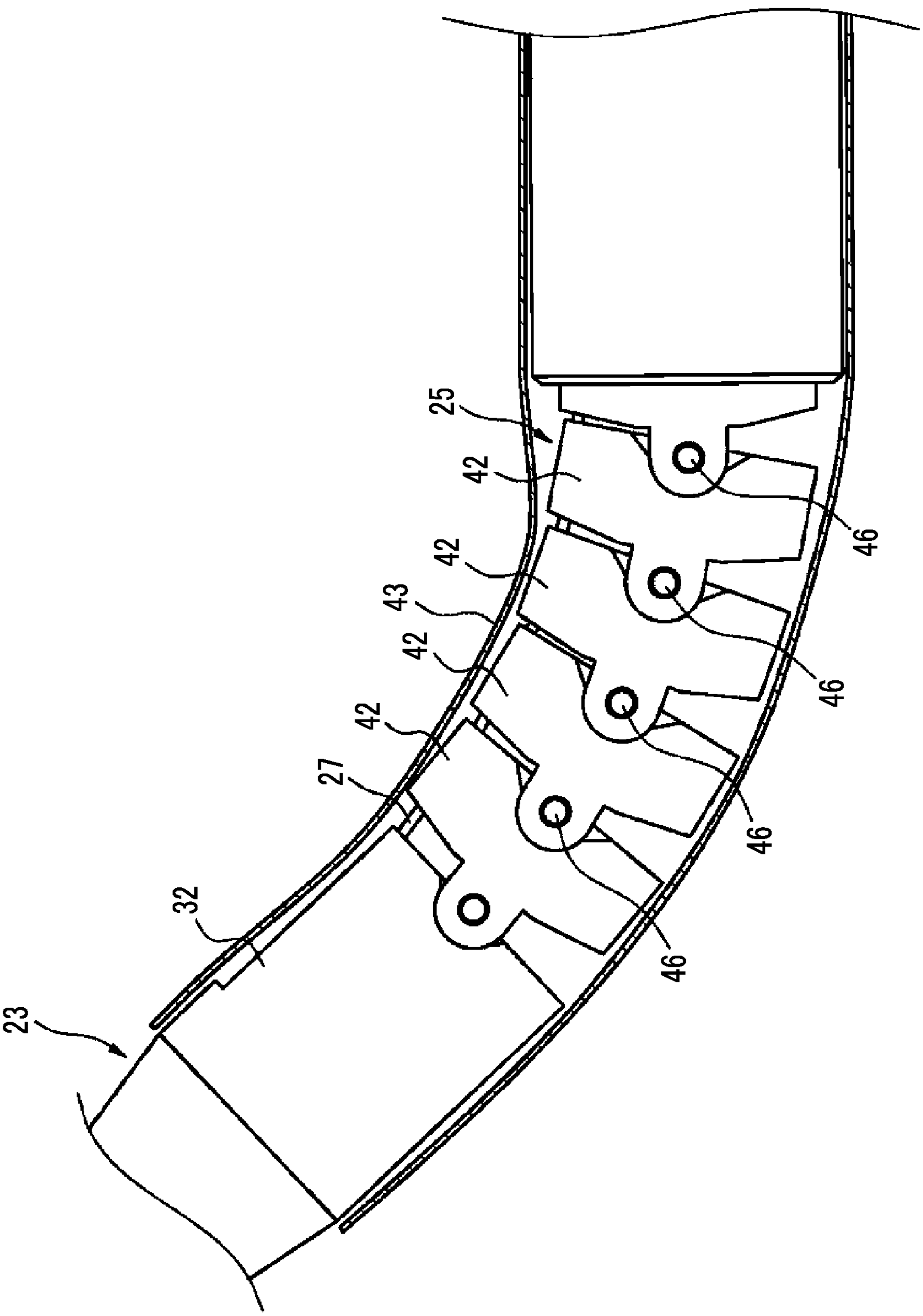
FIG. 9 is a view showing an operation inside the bendable part of FIG. 5.

FIGS. 7 to 9 show a configuration and an operation inside the bendable part 25.

The bendable part 25 has a plurality of bending pieces 42 and an outer coat 43 made of a resin. The plurality of bending pieces 42 are disposed to be arranged in a longitudinal direction of the insertion part 21 including the bendable part 25. The two bending pieces 42 adjacent to each other are coupled to each other via a pair of pins 46 disposed to face each other in a radial direction of the bendable part 25. As shown in FIG. 8, the pair of pins 46 are disposed on an axis X substantially parallel to the opening and closing direction of the pair of grip claws 30. Therefore, the bending pieces 42 that are coupled to be adjacent to each other by the pair of pins 46 are movable rotationally about the axis X which is a rotational axis. By adding rotational movements of the plurality of bending pieces 42 about the axis X which is a rotational axis, the bendable part 25 is bent along the direction (the bending operation plane) substantially perpendicular to the opening and closing direction (a direction of the axis X) of the pair of grip claws 30 as shown in FIG. 9.

The bendable part 25 is bent by the operation wire 27 for opening and closing the pair of grip claws 30. As shown in FIG. 8, each of the plurality of bending pieces 42 has a wire guide 47 that holds the operation wire 27 in a pushable and pullable manner. In a case where each of the bending pieces 42 is divided into two sides including a first side A and a second side B, which is an opposite side, with the axis X as a boundary, the wire guide 47 is provided on one side, which is the second side B. Therefore, as the operation wire 27 is pulled to the operating part 22 side, the bendable part 25 is bent such that the first side A is positioned outside the curve and the second side B is positioned inside the curve.

In this manner, a closing operation of the grip part 24 and a bending operation of the bendable part 25 are performed by pulling the single operation wire 27. Accordingly, an operation of the operating part 22 is easy. Herein, in a case where the operation wire 27 is pulled to the operating part 22 side, the grip part 24 is first closed, and the bendable part 25 is configured to bend in a state where the grip part 24 is closed. An operation sequence of the closing operation of the grip part 24 and the bending operation of the bendable part 25 can be set according to a relationship as to which one of an operation resistance in a case of closing the grip part 24 or an operation resistance in a case of bending the bendable part 25 is greater or smaller. In short, in a case where the operation resistance of the bendable part 25 is relatively great, the closing operation of the grip part 24 comes first, and the bending operation of the bendable part 25 comes later.

The operation resistance in a case where the grip part 24 is closed includes friction at the intersecting portion of the pair of grip claws 30 and friction at a coupling portion between the grip claw 30 and the link member 31. Similarly, the operation resistance in a case where the bendable part 25 bends includes friction at a coupling portion between the two bending pieces 42 adjacent to each other. In addition, the outer coat 43 of the bendable part 25 is an elastic member that linearly extends the bendable part 25, and the operation resistance in a case where the bendable part 25 bends includes elasticity of the outer coat 43. The operation wire 27 is also an elastic member that linearly extends the bendable part 25, and the operation resistance in a case where the bendable part 25 bends includes elasticity of the operation wire 27. The elastic member that extends the bendable part 25 linearly is not limited to the outer coat 43, the operation wire 27, and the like and may be a wire spring, a leaf spring, or the like.

As described above, in the bendable part 25 that is bent by the pulling of the operation wire 27, an elastic force in a direction returning from a bent state to a linear state is generated by the outer coat 43 as the outer coat 43 is made of the elastic member.

In addition, since the outer coat 43 is made of the elastic member, the bendable part 25 generates an elastic force in a restoring direction from a state of being pulled and deformed by the operation wire 27, and the elastic force of the bendable part 25 increases according to a bending amount. Friction adjusting mechanisms 70 and 73 to be described later, which can respond to the elastic force, increase a frictional force according to a bent amount (an angle) of the bendable part 25, and the bent state of the bendable part 25 is well maintained.

Herein, as a movement amount by which the operation wire 27 is pulled increases, a force pulling in a direction of restoring the operation wire 27 (a linearly extending force) increases. In the present embodiment, the friction adjusting mechanisms 70 and 73 to be described later, which can respond to a change in the force pulling in the direction of restoring the operation wire 27 (the elastic restoration force), can increase a frictional force to correspond to a pulled amount of the operation wire 27, and a pulled state can be maintained well.

In addition, the bendable part 25 may be formed of a flexible pipe material made of an elastic material such as an elastomer, instead of the plurality of bending pieces 42 that are members inside the outer coat 43 and that are coupled to be movable rotationally. In a case where the bendable part 25 consists of the flexible pipe material, the operation resistance (the elastic restoration force) in a case where the bendable part 25 bends includes elasticity of the pipe material, and a stronger elastic force is generated. As described above, as the member inside the outer coat 43 is made of an elastic material, the bendable part 25 can generate a biasing force in the restoring direction in a state of being pulled and deformed by the operation wire 27.

Figure 10:
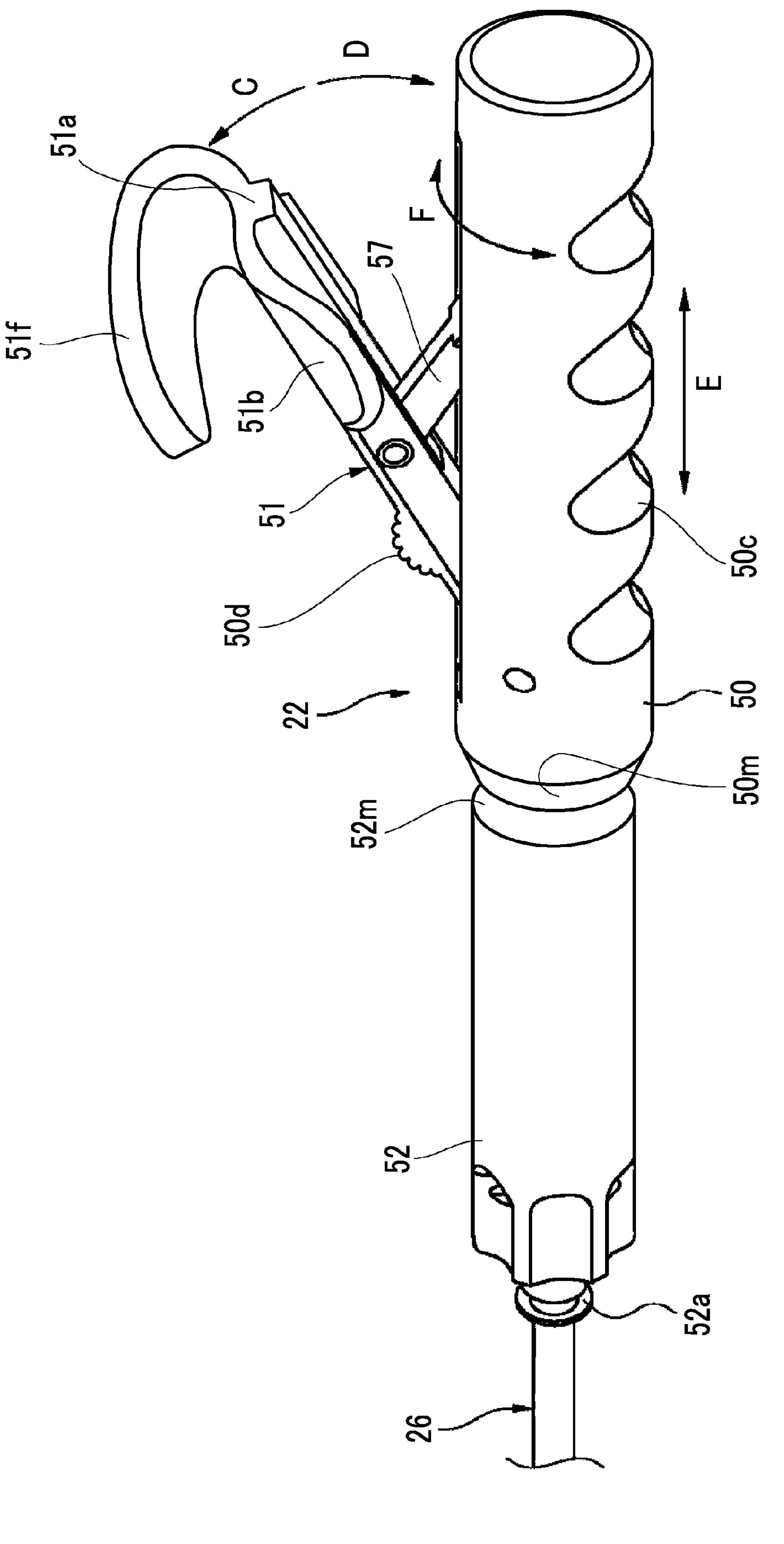
FIG. 10 is a view showing a configuration of an operating part of the endoscope treatment tool of FIG. 2.
Figure 11:
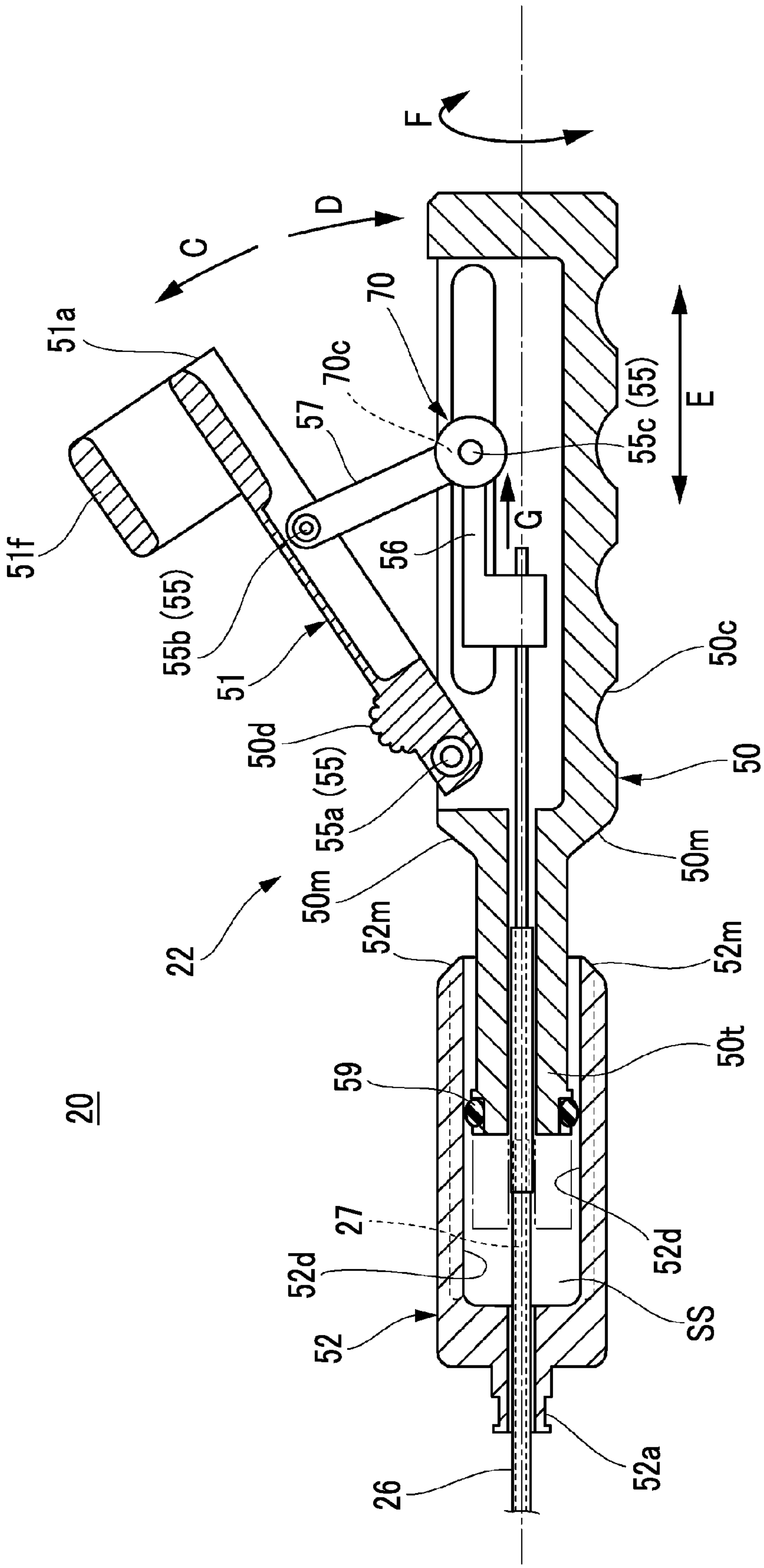
FIG. 11 is a cross-sectional view of the operating part of the endoscope treatment tool of FIG. 2.

FIGS. 10 and 11 show a configuration of the operating part 22.

The operating part 22 has an operating part body 50 that is an input unit for a forward and backward movement/rotation operation of moving the grip part 24 (see FIG. 3) forward and backward and rotating the grip part, an operation handle 51 that is an input unit for an opening/closing/bending operation of opening and closing the grip part 24 and bending the bendable part 25 (see FIG. 2), and the fixing unit 52 that is an attachment portion which is attachably and detachably attached to the endoscope operating part 7 (see FIG. 1).

The fixing unit 52 has a connection fitting **52*a*. The connection fitting 52*a* is connected to a base provided in the first treatment tool insertion opening 13 (see FIG. 1) of the endoscope operating part 7. In a state where the connection fitting 52*a* is connected, the operating part 22 is supported by the endoscope operating part 7**.

The operating part body 50 is formed in a rod shape and is supported by the fixing unit 52 so as to be operable in a central axis direction indicated with an arrow E and a rotation direction around a central axis indicated with an arrow F. The connecting part 26 is connected to the operating part body 50 through the fixing unit 52 and is moved forward and backward along a longitudinal axis of the connecting part 26 in response to an operation of the operating part body 50 in an arrow E direction. In addition, the connecting part 26 is rotated about the longitudinal axis of the connecting part 26 in response to an operation of the operating part body 50 in an arrow F direction. The forward and backward movement and rotation of the connecting part 26 are transmitted to the grip part 24, and the grip part 24 is also moved forward and backward and is rotated integrally with the connecting part 26.

The operation handle 51 is swingably supported by the operating part body 50. Specifically, as shown in FIG. 11, the operation handle 51 is supported by a rotational movement support shaft part **55*a* (55), and a free end portion 51*a* is swingable in an opening direction C being spaced apart from the operating part body 50 and a closing direction D approaching the operating part body 50. In short, the operation handle 51 is supported to move on a fan-shaped operation movement plane centered on the rotational movement support shaft part 55*a***.

Figure 12:
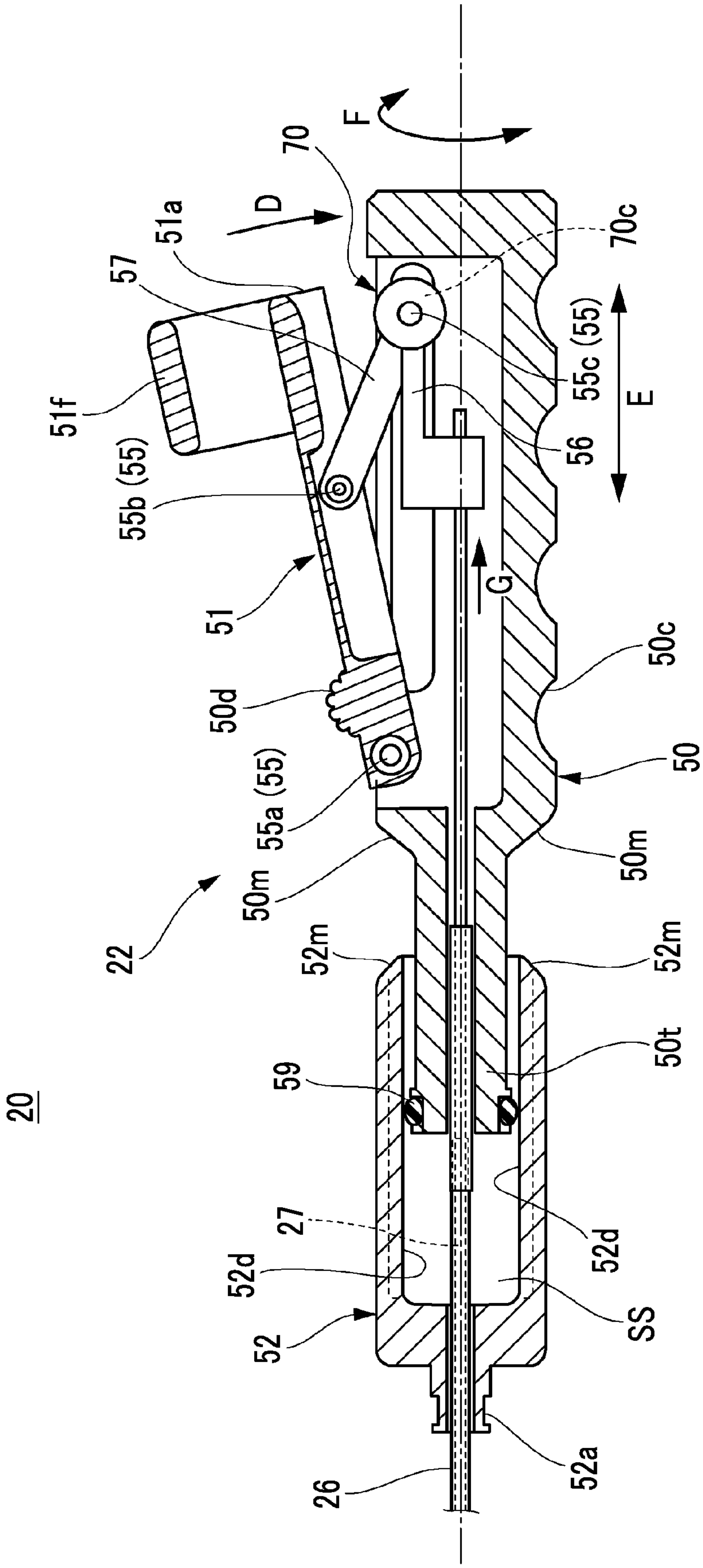
FIG. 12 is a cross-sectional view of a closed state of the operating part of the endoscope treatment tool of FIG. 2.

FIG. 12 shows a state in a case where the operation handle 51 is operated in the closing direction D. The operation handle 51 pulls (the arrow G direction) the operation wire 27 in a case of swinging in the closing direction D and pushes (an opposite direction to an arrow G) the operation wire 27 in a case of swinging in the opening direction C. The operation wire 27 is fixed to a wire holding part 56 provided to be slidably movable along an axis thereof in the operating part body 50. The wire holding part 56 is connected to the operation handle 51 via a link member 57 coupled to a rotational movement support shaft part **55*c* (55) to be movable rotationally. The link member 57 and the operation handle 51 are connected to each other to be movable rotationally via a rotational movement support shaft part 55*b* (55**).

Herein, as described above, as the pulled amount of the operation wire 27 (a movement amount in the arrow G direction) increases, a force restoring the wire holding part 56 (an elastic restoration force) increases. In addition, in a case where a lesion part is gripped and lifted, a restoration force becomes stronger with a lifted amount (a pulled amount). Therefore, a restoration force that increases with an increase in the pulled amount acts on the operation handle 51. In order to respond to a change in the restoration force, the friction adjusting mechanism 70 that increases a frictional force for locking the wire holding part 56 to correspond to the pulled amount of the operation wire 27 that is interlocked with an operation of the operation handle 51 is provided at the rotational movement support shaft part **55*c***.

The operation wire 27 is pushed out to the distal end part 23 side in response to swinging of the operation handle 51 in the opening direction C and is pulled to the operating part 22 side in response to swinging of the operation handle 51 in the closing direction D. In this case, as the operation handle 51 swings in the closing direction D, the grip part 24 is closed and the bendable part 25 is bent.

As the operation handle 51 has the friction adjusting mechanism 70 that maintains an operation state thereof, the operation handle 51 is configured to be capable of maintaining a bending angle of the bendable part 25 at any one of angles that are equal to or smaller than a maximum bending angle. The friction adjusting mechanism 70 increases a frictional force for locking the wire holding part 56 to correspond to an increase in the pulled amount of the operation wire 27 caused by the wire holding part 56 that is interlocked with swinging of the operation handle 51.

As described above, since the friction adjusting mechanism 70 can increase a frictional force as the pulled amount of the operation wire 27 increases, the restoring movement of the operation handle 51 is prevented even in a case where a wire restoration force becomes stronger by increasing the pulled amount of the operation wire 27, a hand can be released from the operation handle 51 even in a case of any operation position of the operation handle 51, an operation force in a case of a rotational movement is small, and a stable operation is possible.

As the wire holding part 56 is coupled to be slidably movable via the link member 57, a large number of parts of the operation handle 51 move relatively with an operation of the operation handle 51. Accordingly, options of a part where the friction adjusting mechanism 70 is to be provided can be increased. In addition, as the amount of a pulling force with respect to the wire holding part 56 increases, the link member 57 is inclined such that an inclined angle on the distal end part 23 side with respect to the wire holding part 56 decreases. Thus, a force against the restoration force of the operation wire 27 can be increased, and this can be used in handle operability.

Figure 13:
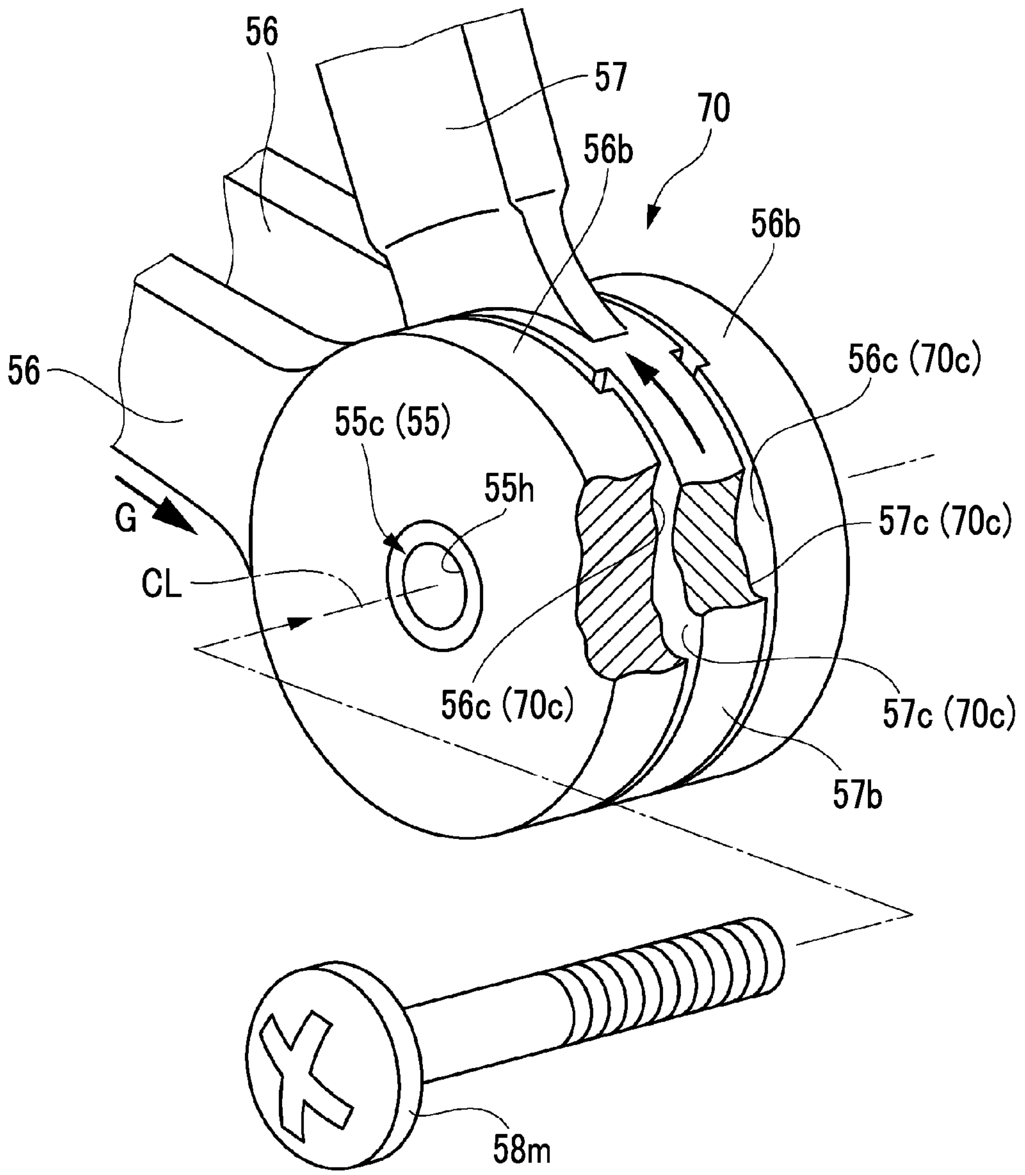
FIG. 13 is an enlarged perspective view of a friction adjusting mechanism shown in FIG. 11.
Figure 14:
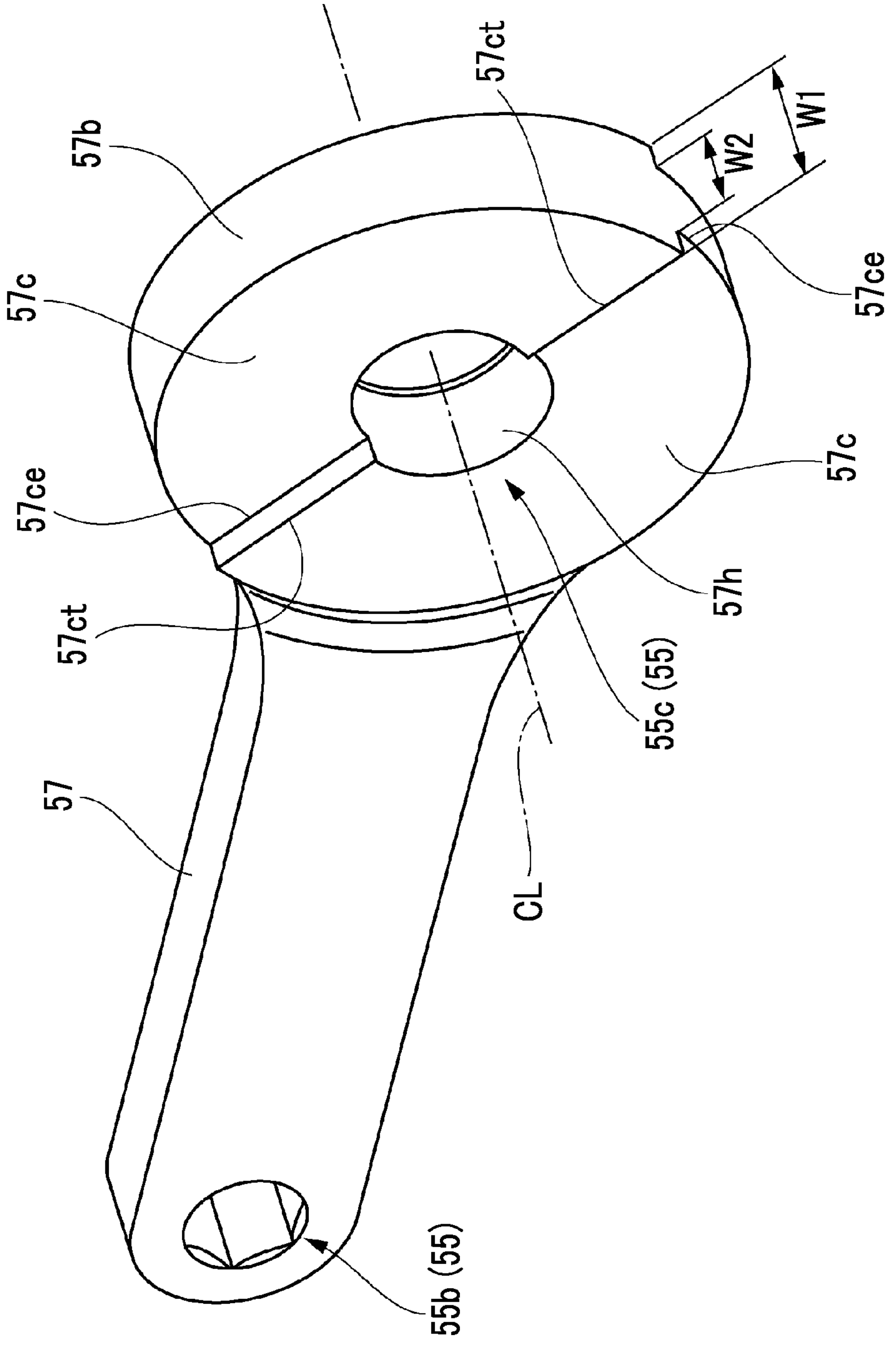
FIG. 14 is an exploded perspective view of a link member shown in FIG. 11.
Figure 15:
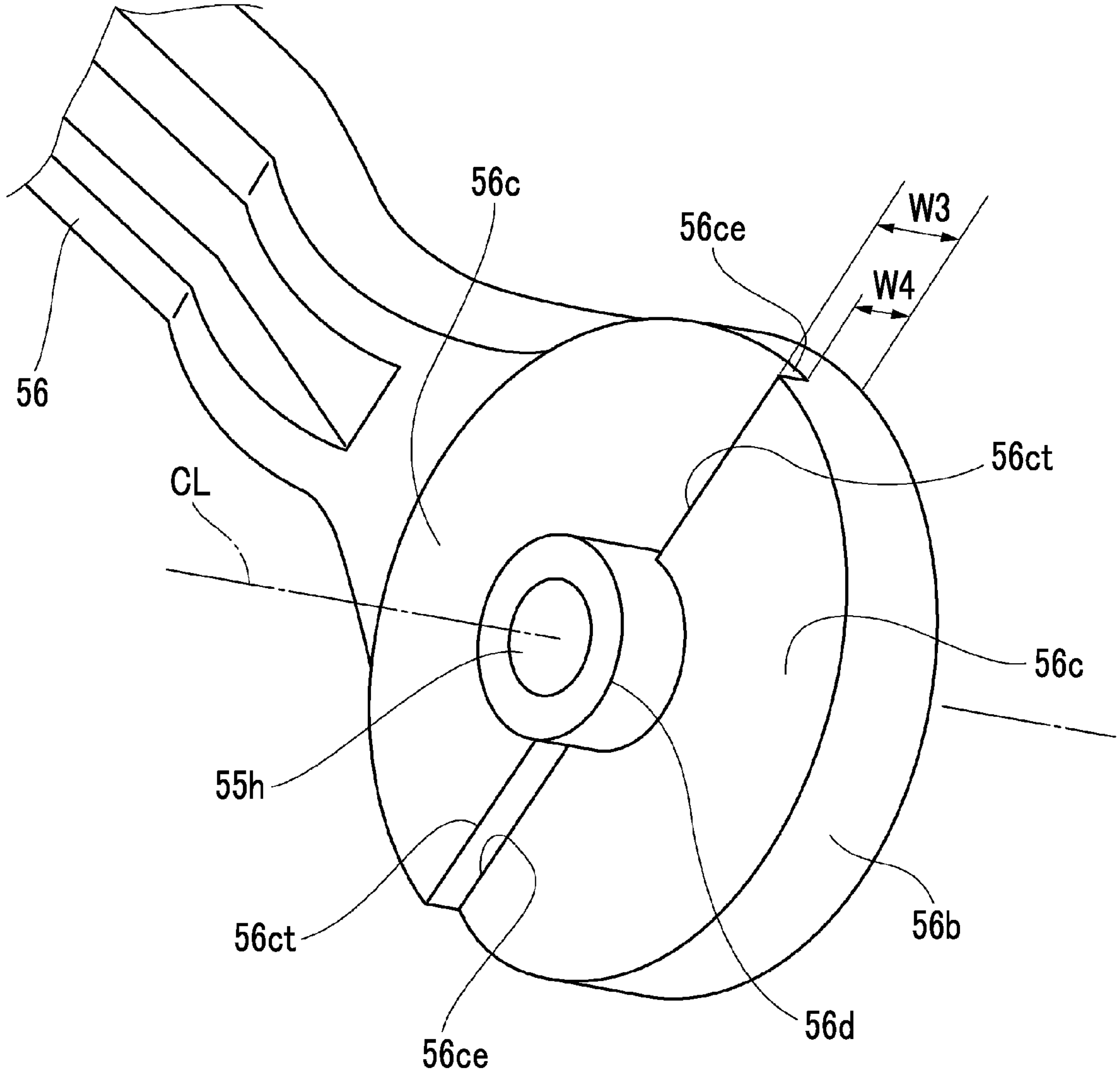
FIG. 15 is an exploded perspective view of a wire holding part shown in FIG. 11.

FIGS. 13 to 15 are perspective views showing an example of the friction adjusting mechanism 70. As shown in FIG. 13, the friction adjusting mechanism 70 is fastened by a fastening member 58*m* that penetrates a through-hole 55*h* of the rotational movement support shaft part 55*c* such that the link member 57 is sandwiched between the pair of wire holding parts 56 (a female thread side of the fastening member 58*m* is omitted in FIG. 13). Herein, in the wire holding part 56 and the rotational movement support shaft part 55*c* of the link member 57, a peripheral portion around the shaft is configured in a cylindrical shape. In addition, cam parts 70*c* that can adjust a frictional force by facing and coming into contact with each other in a member thickness direction of a cylindrical part are provided. As will be described later, the cam parts 70*c* can change a contact pressure between members to correspond to a rotation angle of the rotational movement support shaft part 55*c*.

As shown in FIG. 14, in the link member 57, cam parts 57*c* (70*c*) are provided at both front and back edge surfaces of a cylindrical portion 57*b* that has a link portion through-hole 57*h* of the rotational movement support shaft part 55*c* in a case of being viewed from an axial center CL direction. The cam parts 57*c* are formed to divide both front and back edge surfaces of the cylindrical portion 57*b* into semi-circular regions. In short, at both front and back edge surfaces of the cylindrical portion 57*b*, a cam surface inclined in a circumferential direction is formed for each semi-circular region. More specifically, an inclined structure, in which with respect to a thickness (W1) of one end side 57*ct* in the semi-circular region of the cylindrical portion 57*b*, a thickness (W2) of the other end side 57*ce* decreases, is adopted. That is, a structure, in which the thickness of the cylindrical portion 57*b* gradually decreases toward a counterclockwise direction in FIG. 14 with the thickness (W1) of the one end side 57*ct* as maximum, is adopted.

As shown in FIG. 15, a cylindrical portion 56*b* of the wire holding part 56 has a boss part 56*d* that has the through-hole 55*h* and that can be engaged with the link portion through-hole 57*h*, and a cam part 56*c* is provided on one edge surface side (an inside) at a portion around the boss part 56*d* in a case of being viewed from the axial center CL direction. The cam part 56*c* comprises a cam surface that is divided into semi-circular regions of the cylindrical portion 56*b* and that has a thickness inclined in a circumferential direction in the semi-circular regions. A cam surface is adopted such that the thickness of the cylindrical portion 56*b* gradually decreases toward a thickness (W4) of the other end part 56*ce* in a clockwise direction in FIG. 15 with a thickness (W3) of one end side 56*ct* as maximum.

As the cam part 56*c* of the wire holding part 56 configured as described above and the cam part 57*c* of the link member 57 are combined with each other as shown in FIG. 13 and are fastened to each other by the fastening member 58*m*, a contact pressure between the cam surfaces can be changed. That is, in a case where the link member 57 is moved rotationally about the rotational movement support shaft part 55*c* in a direction in which the angle of the link member 57 with respect to the wire holding part 56 decreases (in a case where the pulled amount increases), the cam part 57*c* of the link member 57 acts to spread out the cam part 56*c* of the wire holding part 56. As a result, a contact pressure between cam surfaces can become stronger gradually with an increase in the pulled amount of the operation wire 27, and a frictional force can be gradually increased.

As described above, since the friction adjusting mechanism 70 is provided at the rotational movement support shaft part 55*c* that supports the operation handle 51 to be movable rotationally and the cam parts 70*c* that can change the contact pressure to correspond to the rotation angle are included around the shaft in the rotational movement support shaft part 55*c*, the structure of the friction adjusting mechanism 70 can be made small without increasing in size.

As described above, the cam parts 70*c* of the friction adjusting mechanism 70 are provided at the wire holding part 56 in the operating part body 50. That is, by being provided at the rotational movement support shaft part 55*c* between the link member 57 and the wire holding part 56, a liquid can be prevented from infiltrating into the cam parts 70*c*, for example, even in a case where an operator's hand is wet, and fluctuations in the frictional force can be prevented.

In addition, the fastening member 58*m* that penetrates the rotational movement support shaft part 55*c* is provided in the rotational movement support shaft part 55*c*, and the fastening force of the rotational movement support shaft part 55*c* is configured to be adjustable. As described above, as the fastening force is adjustable through fastening and adjusting of the fastening member 58*m*, the contact pressure between the cam surfaces can be changed. As a result, the frictional force of the friction adjusting mechanism 70 can be easily adjusted. In addition, the contact pressure between cam surfaces can be adjusted by providing an elastic member to be sandwiched between the fastening member 58*m* and the wire holding part 56. For example, by providing a spring washer having a small spring constant to be sandwiched between the fastening member 58*m* and the wire holding part 56, a rise in the contact pressure can be moderated.

The friction adjusting mechanism 70 is configured to be provided at the rotational movement support shaft part 55*c*, but may be configured to be provided at other rotational movement support shaft parts 55*a* and 55*b*. In short, the friction adjusting mechanism 70 may be provided at any locations insofar as the locations are at the rotational movement support shaft part 55 that involves in swinging of the operation handle 51, and the friction adjusting mechanism 70 may be provided at a plurality of locations. In addition, a structure, in which while the friction adjusting mechanism 70 is at one location, a friction member that generates a constant frictional force regardless of the operation position of the operation handle 51 and that is made of, for example, rubber or the like is disposed at the other location, may be adopted.

It is desirable that materials for the link member 57 and the wire holding part 56, which configure the cam part 70*c*, are materials that are unlikely to cause the stick slip phenomenon while causing appropriate friction. In addition, since the wire holding part 56 slides on the operating part body 50, a material having a low friction coefficient is desirable. From the above perspective, a low-friction resin material, such as polypropylene, polyethylene, and polytetrafluoroethylene (PTFE), is suitable for the wire holding part 56, and a material having an appropriate friction coefficient, such as acrylonitrile butadiene styrene (ABS), is suitable for the link member 57.

In transport and storage states, a lever is fixed in a state where a contact pressure between cams is small. Accordingly, applying a long-term compressive force to a component configuring the cam can be avoided, and a dimension change and a decrease in the contact pressure caused by the creep phenomenon can be suppressed.

Figure 16:
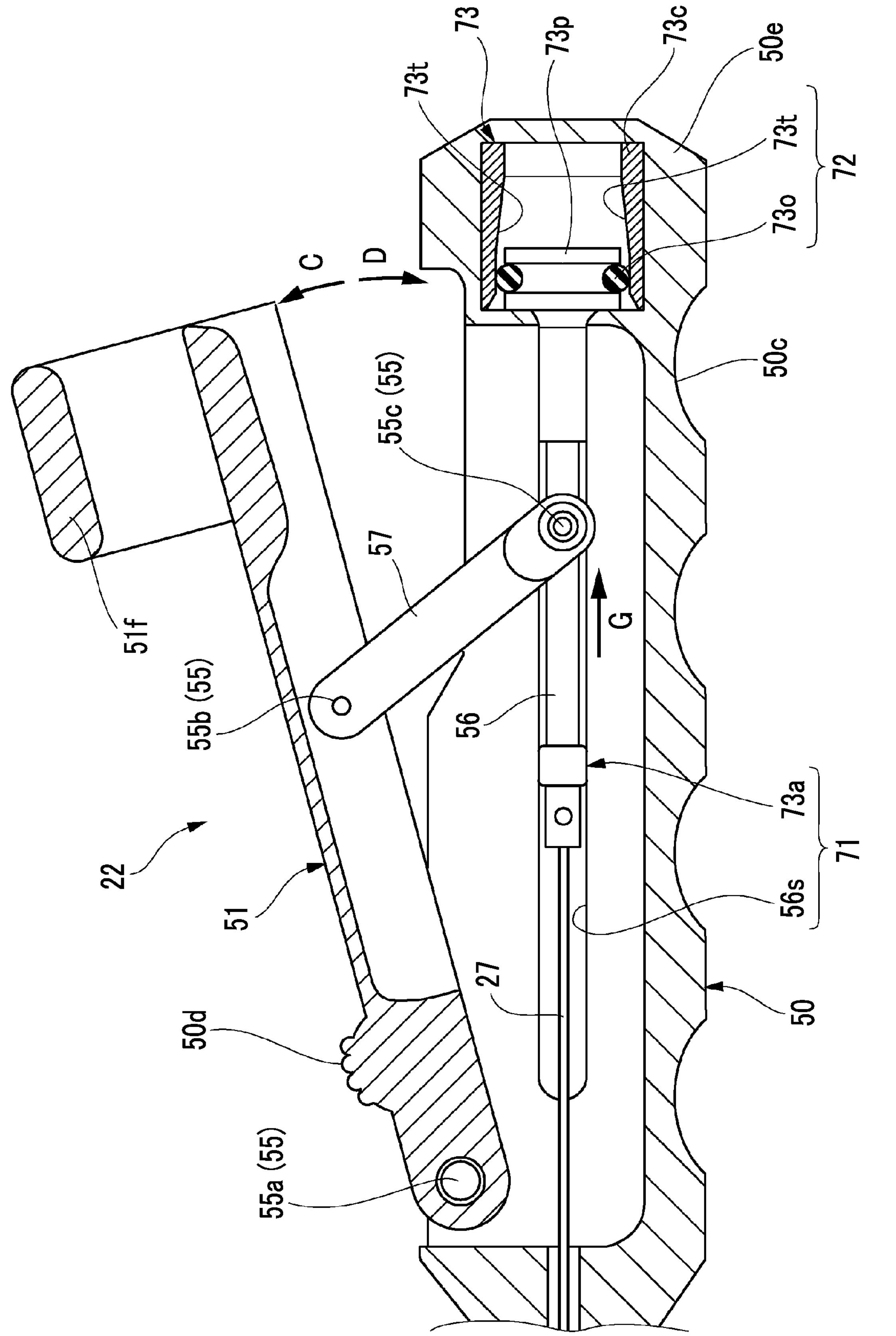
FIG. 16 is a cross-sectional view of an example of another friction adjusting mechanism of the operating part of the endoscope treatment tool.

FIG. 16 is a cross-sectional view of an example of another friction adjusting mechanism 73 of the operating part 22. As shown in FIG. 16, the friction adjusting mechanism 73 comprises a first sliding portion 71 and a second sliding portion 72 that are sliding portions slidingly contactable with the wire holding part 56 with a sliding movement of the wire holding part 56 which slidingly moves with respect to the operating part body 50. The first sliding portion 71 has, for example, a shaft-shaped flat sliding wall surface 56*s* that slidably holds the wire holding part 56. The second sliding portion 72 has an inclined wall surface 73*t* that can increase the pulled amount of the operation wire (the movement amount of the wire holding part 56) and increase the retention power of the wire holding part 56.

As described above, the friction adjusting mechanism 73 includes the first and second sliding portions 71 and 72 that are slidingly contactable with the wire holding part 56 which slidingly moves with respect to the operating part body 50 in response to the movement of the wire holding part 56, and the first and second sliding portions 71 and 72 have an inclined structure in which at least a part thereof increases a contact pressure on the wire holding part 56 to correspond to an increase in the pulled amount of the operation wire 27. Accordingly, it is possible to increase a frictional force as the pulled amount of the operation wire 27 increases. Therefore, even in a case where the pulled amount of the operation wire 27 increases and a wire restoration force becomes stronger, a contact force can be gradually increased by the inclined wall surface 73*t* to correspond to the strength of a restoration force of the operation handle 51. As a result, the operation handle 51 is held no matter where an operation position thereof is, and a stable operation is possible.

For example, the first sliding portion 71 is configured such that for example, a ring-shaped member 73*a* such as an O-ring is in contact with the sliding wall surface 56*s* configured by a cylindrical inner wall surface along a sliding direction. Therefore, since the sliding wall surface 56*s* and the ring-shaped member 73*a* are in contact with each other with a constant contact force at all times, the first sliding portion 71 can generate a constant frictional force with respect to the wire holding part 56.

As described above, since the sliding portion includes the first sliding portion 71 having a substantially constant contact pressure with respect to the wire holding part 56 and the second sliding portion 72 having an inclined structure in which a contact pressure with respect to the wire holding part 56 increases to correspond to an increase in the pulled amount of the operation wire 27, a frictional force can be separately adjusted by the two sliding portions, and the frictional force can be easily adjusted. Accordingly, a frictional force can be stably generated, and even in a case where a wire restoration force becomes stronger as the pulled amount of the operation wire 27 increases, the operation handle 51 can be reliably held. Thus, a stable operation is possible no matter where the operation position of the operation handle 51 is.

The second sliding portion 72 comprises, for example, a cylindrical cylinder 73*c* that is provided on one end side 50*e* of the operating part body 50 and a piston 73*p* that is provided at one end part of the wire holding part 56 and that is provided to be slidably movable in the cylinder 73*c*. For example, a ring-shaped elastic member 73*o* that is in contact with the inclined wall surface 73*t* configuring an inner wall surface of the cylinder 73*c*, such as an O-ring, is provided on an outer periphery of the piston 73*p*. The inclined wall surface 73*t* is inclined such that a cylinder inner diameter decreases as the piston 73*p* moves in a pulling direction (moves in the arrow G direction in the drawings).

Herein, the first sliding portion 71 is set to have a frictional force smaller than the frictional force of the second sliding portion 72. Accordingly, a minimum frictional force can be generated by the first sliding portion 71, and frictional force adjustment can be performed by the second sliding portion 72. As a result, the frictional force is easily adjusted, and a stable frictional force can be obtained.

In addition, a frictional force can be adjusted by a contact force between the inclined wall surface 73*t* and the elastic member 73*o* of the second sliding portion 72. Further, since the elastic member 73*o* is made of an O-ring, an elastic deformation structure can be easily formed and can be manufactured at low costs.

Figure 17:
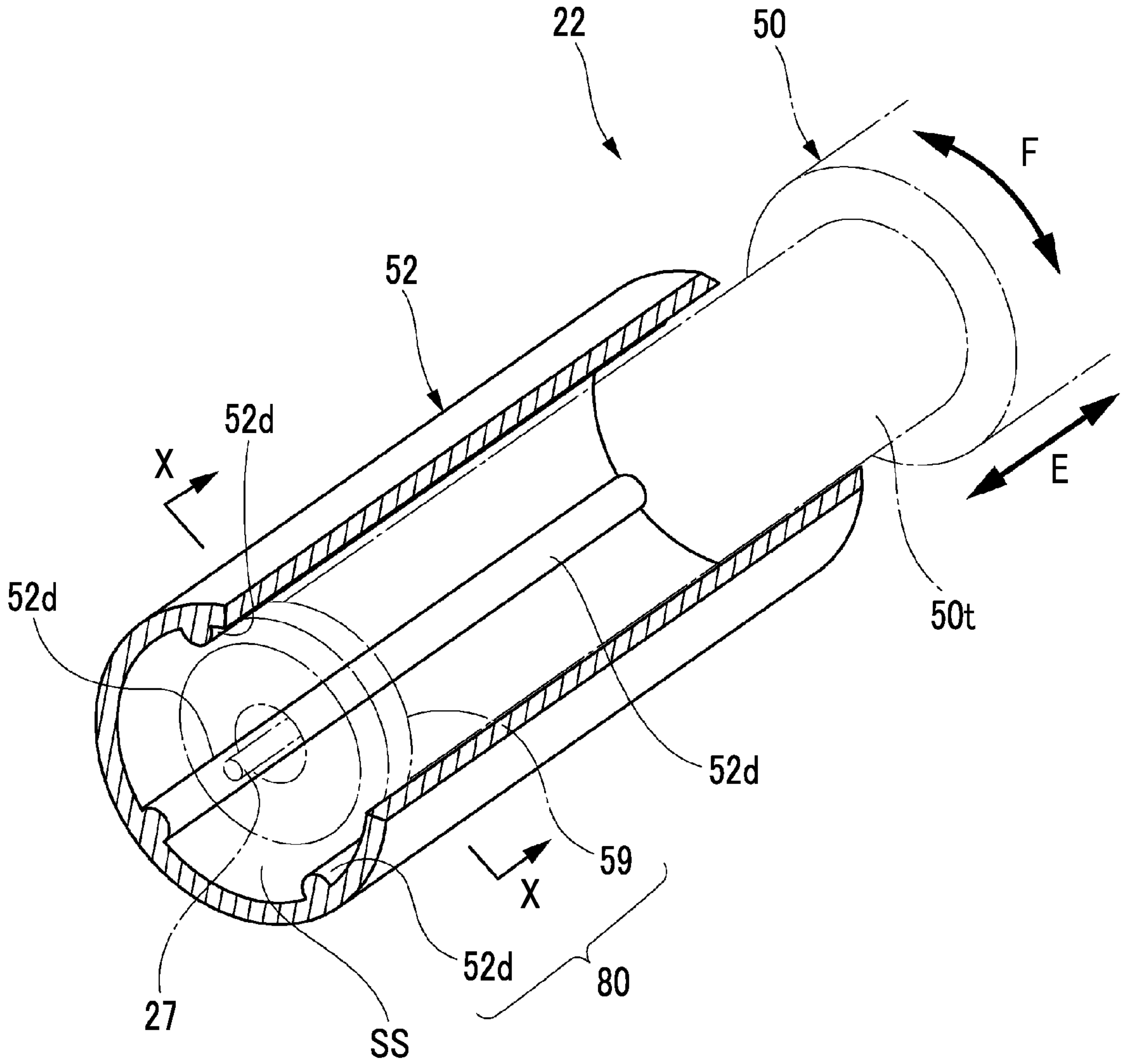
FIG. 17 is an exploded perspective view showing a friction mechanism that generates a frictional force between a fixing unit and an operating part body in the operating part of the endoscope treatment tool.
Figure 18:
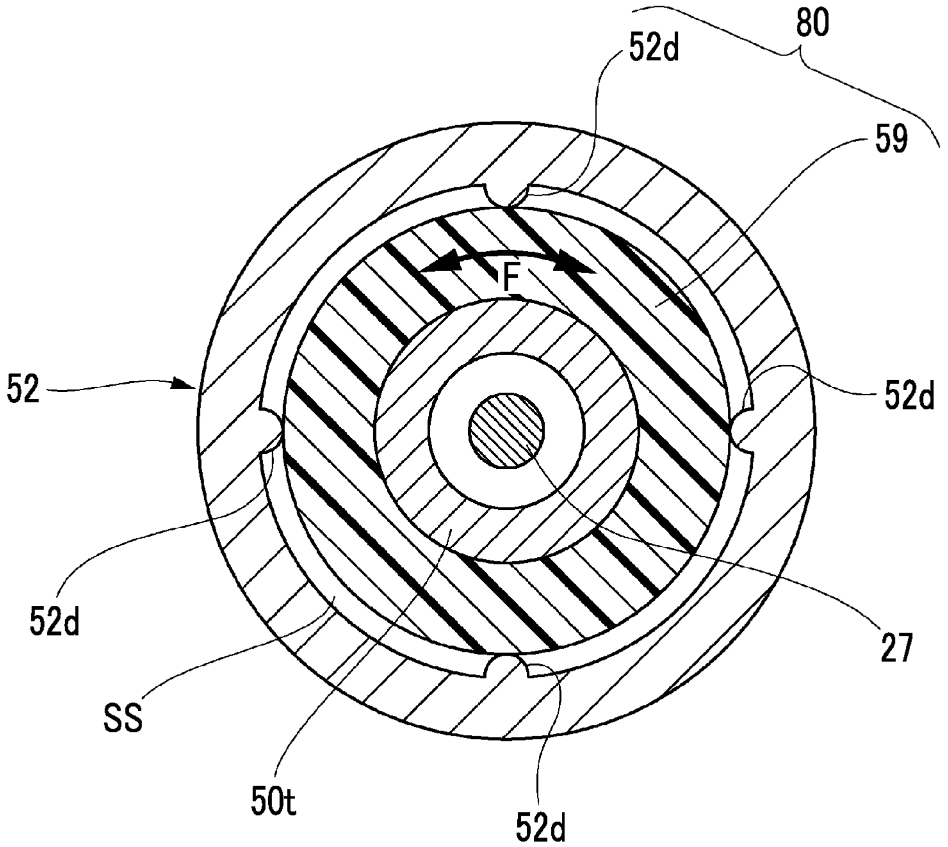
FIG. 18 is a cross-sectional arrow view of a portion taken along line X-X of FIG. 17.
Figure 19:
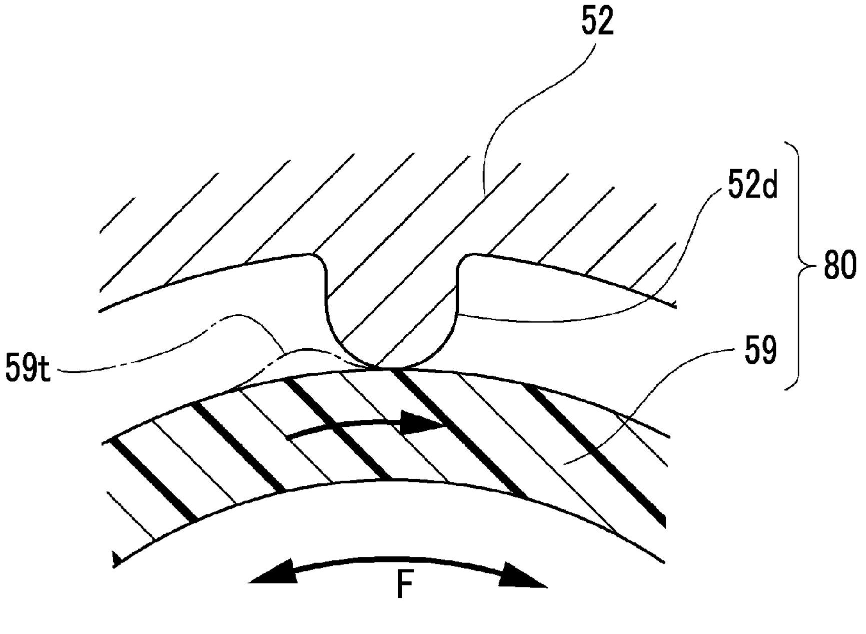
FIG. 19 is an enlarged cross-sectional view for describing a contact state of the friction mechanism shown in FIG. 18 in a case of rotation.

FIG. 17 is an exploded perspective view showing a friction mechanism 80 that generates a frictional force between the fixing unit 52 and the operating part body 50. In addition, FIG. 18 shows an internal structure of the fixing unit 52 and is a cross-sectional arrow view of a portion taken along line X-X of FIG. 17. In addition, FIG. 19 is an enlarged cross-sectional view for describing a contact state of the friction mechanism 80 in a case of rotation.

As shown in FIGS. 17 and 18, the fixing unit 52 that attaches the operating part 22 to the endoscope operating part 7 (see FIG. 1) comprises a substantially cylindrical accommodation space SS that accommodates an insertion end part 50*t* having a small diameter on a distal end side (the left in FIG. 17) of the operating part body 50 to be slidably movable. A protrusion 52*d* that protrudes radially inward of the accommodation space SS is provided on an inner wall surface configuring the accommodation space SS. The protrusion 52*d* is formed along a longitudinal direction of the accommodation space SS, that is, a forward and backward movement direction of the insertion end part 50*t* (a pulling direction and a pushing direction of the operation wire 27). In addition, a plurality of (four) protrusions 52*d* are provided at predetermined intervals in a circumferential direction of the inner wall surface. An annular friction member 59 is provided at the insertion end part 50*t* in a rotation direction of the insertion end part 50*t* (the arrow F direction) to be in contact with the protrusions 52*d* at a predetermined contact pressure. The friction member 59 is made of, for example, a member having predetermined elasticity, such as an O-ring.

As described above, the operating part 22 includes the fixing unit 52 that attaches the operating part 22 and the operating part body 50 that is capable of moving forward and backward with respect to the fixing unit 52 along the operation wire 27 and that is rotatable along a plane orthogonal to a forward and backward movement direction. In addition, the operating part 22 comprises the friction mechanism 80 that generates a first frictional force between the fixing unit 52 and the operating part body 50 in a rotation direction (a frictional force in the rotation direction) and a second frictional force between the fixing unit 52 and the operating part body 50 in a forward and backward movement direction (a frictional force in the forward and backward movement direction), which is different from the first frictional force.

In short, the friction mechanism 80 generates a first frictional force in a direction of the rotation (the arrow F direction) of the operating part body 50 with respect to the fixing unit 52 (a frictional force in the rotation direction). In addition, a second frictional force in the forward and backward movement direction (the arrow E direction) of the operating part body 50 with respect to the fixing unit 52 (a frictional force in the forward and backward movement direction), which is different from the first frictional force, is generated.

As described above, as a frictional force in the rotation direction in a case of the rotation and a frictional force in the forward and backward movement direction in a case of the forward and backward movement are different between the fixing unit 52 and the operating part body 50, the operating part 22 can be separately set for the force in the rotation direction and the force in the forward and backward movement direction. Accordingly, by giving a priority to any one of the rotation or the forward and backward movement as in the related art, a situation that deteriorates operability of the other can be avoided. As a result, the operating part 22, in which both of the rotation and the forward and backward movement of the operating part body 50 are easy, can be provided.

As shown in FIG. 19, a first frictional force that is generated by a relative movement between the friction member 59 and the protrusion 52*d* in the rotation direction and increases as a deformation part 59*t* is generated at the friction member 59. This is because in a case where the friction member 59 rotates with respect to the protrusion 52*d*, the deformation part 59*t* is formed under conditions such as the surface of the friction member 59 being slightly recessed by a contact pressure with the protrusion 52*d*, the friction member 59 being easily deformed (easily extended) in the circumferential direction by being rubbed with the protrusion 52*d*, and the friction member 59 being easily extended in the rotation direction since the friction member 59 becomes longer through rotation. As the deformation part 59*t* is formed, the friction member 59 has a high contact pressure with respect to the protrusion 52*d* and a great friction resistance.

On the other hand, the surface of the friction member 59 is recessed with respect to the protrusion 52*d* in the forward and backward movement direction. In a state of being recessed in a radial direction (a thickness direction) of the friction member 59, a portion such as the deformation part 59*t* is not formed, and a second frictional force does not increase. That is, a first frictional force is set to be larger than the second frictional force.

As described above, as a first frictional force, which is a frictional force in the rotation direction, is set to be larger than a second frictional force, which is a frictional force in the forward and backward movement direction, the first frictional force is adjustable to approach a necessary force in a case of a rotation operation of the operating part 22 and in a case of a forward and backward movement operation, and thereby the operability of the operating part 22 can be improved.

In the friction mechanism 80, the friction member 59 is extended along the rotation direction, and the protrusion 52*d* is extended along the forward and backward movement direction. With the configuration, contact between the friction member 59 and the protrusion 52*d* can increase a resistance in the rotation direction since the protrusion 52*d* moves while deforming the friction member 59 in the rotation direction. Compared to this, since the friction member 59 is in a partial contact state where only a predetermined portion comes into contact with the protrusion 52*d* in the forward and backward movement direction, a resistance in a case of forward and backward movement can be decreased. As a result, each of the resistances in the rotation direction and the forward and backward movement direction can be optimized, and the operability of the operating part body 50 can be improved.

As shown in FIG. 18, the friction member 59 is configured in an annular shape, and the protrusion 52*d* is made of a plurality of protrusions 52*d* that are four protrusions disposed at predetermined intervals in the circumferential direction of the friction member 59 and that extend in the forward and backward movement direction. Accordingly, contact of the friction member 59 with the protrusion 52*d* is partial in the forward and backward movement direction, and thereby an increase in a friction resistance is avoided. On the other hand, since contact between the protrusion 52*d* and the friction member 59 in the rotation direction is accompanied by deformation of the friction member 59 at a location of each protrusion 52*d*, the friction resistance can be increased.

On the contrary, in a case of increasing a friction resistance in the forward and backward movement direction, the width of the protrusion 52*d* may be increased. Since the friction resistance in the forward and backward movement direction is almost proportional to a contact area of the protrusion 52*d* with the friction member 59, the friction resistance can be freely adjusted by changing the shape of the protrusion 52*d*.

Since each of frictional forces in the rotation direction and the forward and backward movement direction can be freely designed with the configuration described above, the use of a lubricant can also be avoided. Also an effect of eliminating a need for the lubricant in terms of quality and costs can be expected since the lubricant is complicated to be managed in manufacturing and becomes causes of various problems, such as variations caused by a coating amount and an adverse effect on a resin material.

Figure 20:
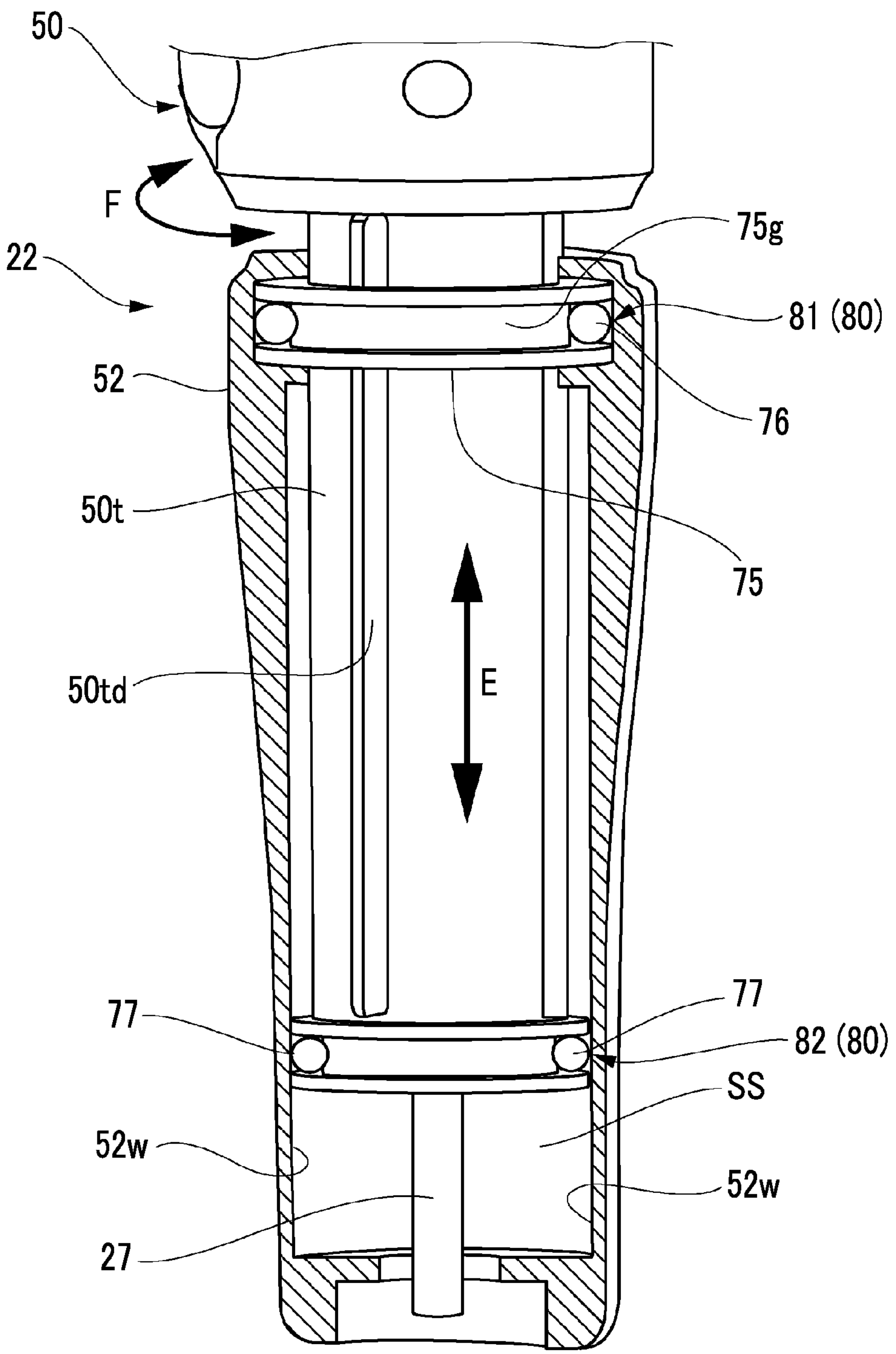
FIG. 20 is a cross-sectional perspective view showing another example of the friction mechanism that generates the frictional force between the fixing unit and the operating part body in the operating part of the endoscope treatment tool.
Figure 21:
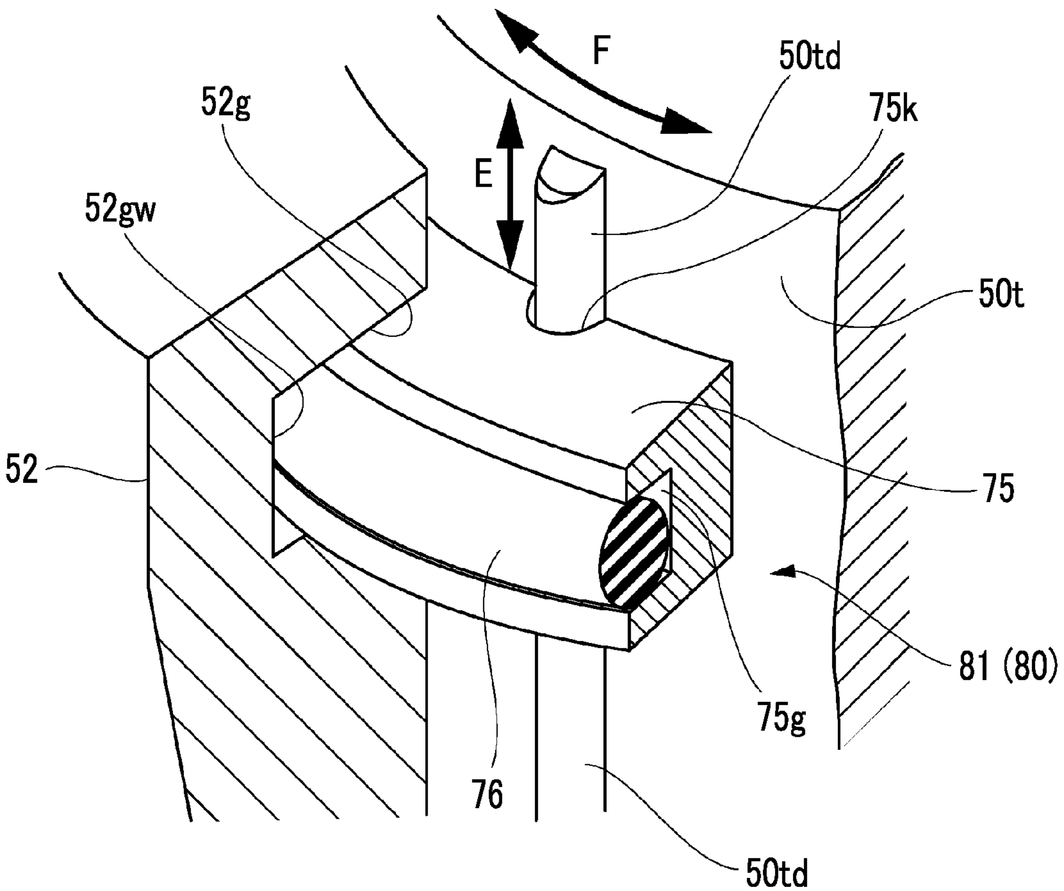
FIG. 21 is an enlarged cross-sectional perspective view of main parts of the friction mechanism shown in FIG. 20.

FIG. 20 is a cross-sectional perspective view showing another example of the friction mechanism 80 that generates a frictional force between the fixing unit 52 and the operating part body 50 in the operating part 22. FIG. 21 is an enlarged cross-sectional perspective view of main parts of the friction mechanism 80 shown in FIG. 20.

The friction mechanism 80 of the operating part 22 shown in FIG. 20 is provided with a slide ring 75, of which a movement in the forward and backward movement direction is regulated, between the fixing unit 52 and the operating part body 50, that is, between the fixing unit 52 and the insertion end part 50*t* of the operating part body 50. The slide ring 75 allows the movement of the operating part body 50 in the forward and backward movement direction on a side fitted to a protrusion 50*td*. On the other hand, a rotation movement (the arrow F direction) of the operating part body 50 via a friction member 76 is allowed on an opposite side to the side fitted to the protrusion 50*td*.

In addition, the friction mechanism 80 is configured by two parts that have a first friction part 81 which is a part having the slide ring 75 and a second friction part 82 which generates frictional forces in the rotation direction and the forward and backward movement direction at a part different from the first friction part 81.

The second friction part 82 has, for example, a structure where an O-ring 77 that is provided at a distal end part of the insertion end part 50*t* and a cylindrical inner peripheral wall surface 52*w* of the fixing unit 52 come into contact with each other. Therefore, in response to the rotation movement (the arrow F direction) of the operating part body 50, predetermined friction occurs. In addition, in response to the forward and backward movement (the arrow E direction) of the operating part body 50, predetermined friction occurs.

As described in FIG. 21, a ring groove 75*g* is formed in the slide ring 75 configuring the first friction part 81 on an outside in a ring radial direction, and the friction member 76 consisting of an O-ring is fitted to the ring groove 75*g*. In addition, the slide ring 75 is fitted to a ring guide groove 52*g* formed along a circumferential direction of an inner surface of the fixing unit 52. Therefore, a bottom wall 52*gw* of the ring guide groove 52*g* and the friction member 76 come into contact with each other. In addition, a vertical groove 75*k* along the forward and backward movement direction is provided on an inner peripheral side of the slide ring 75, and the protrusion 50*td* is slidably fitted to the vertical groove 75*k*. As configured described above, the first friction part 81 hardly generates a resistance caused by a frictional force in the forward and backward movement direction, but can generate a large frictional force in the rotation direction.

As described above, a frictional force between a side in contact with the slide ring 75 and a side in contact with the friction member 76 can be changed by providing the slide ring 75 between the fixing unit 52 and the insertion end part 50*t* of the operating part body 50 and providing the friction member 76 on one end side of the slide ring 75. As a result, friction between the fixing unit 52 and the operating part body 50 in the rotation direction (the arrow F direction) and friction between the fixing unit 52 and the operating part body 50 in the forward and backward movement direction (the arrow E direction) can be distinctly separated.

In addition, by providing a plurality of friction parts including the first friction part 81 and the second friction part 82, a frictional force can be adjusted by the plurality of parts, and thereby adjustment is easy.

In addition, the second friction part 82 is set to generate a frictional force smaller than that of the first friction part 81.

Although a configuration where the protrusion 50*td* is provided at the operating part body 50 has been described in FIGS. 20 and 21, the protrusion 50*td* may be provided at the fixing unit 52. In this case, the ring guide groove 52*g* is provided in the operating part body 50. In addition, the vertical groove 75*k* is provided on an outer peripheral side of the slide ring 75, and the ring groove 75*g* and the friction member 76 are provided on the inner peripheral side of the slide ring 75. That is, the protrusion 50*td* is provided on one of the fixing unit 52 or the operating part body 50 and protrudes to the other side of the fixing unit 52 or the operating part body 50. Specifically, the protrusion 50*td* is provided at the fixing unit 52 (one) and protrudes to a side (the other side) of the operating part body 50, or the protrusion 50*td* is at the operating part body 50 (one) and protrudes to a side (the other side) of the fixing unit 52.

As described above, as the second friction part 82 generates a small frictional force, a minimum frictional force can be generated by the second friction part 82. Accordingly, the frictional force of the first friction part 81 can be easily adjusted.

Referring back to FIG. 10, in a case of operating the operating part body 50 in the forward and backward movement direction, a concave part 50*c* and a convex part 50*d* that can be engaged with fingers are provided at an outer surface of the operating part body 50.

As described above, by providing the concave part 50*c* and the convex part 50*d* at the outer surface of the operating part body 50, in a case of operating the operating part body 50 in the forward and backward movement direction, fingers can be hooked to the concave part 50*c* and the convex part 50*d* that can be engaged therewith, and operability in the forward and backward movement direction can be improved.

In addition, in a state where the operating part body 50 has most approached the fixing unit 52 (the state shown in FIG. 10), an interval between an edge surface 52*m* of the fixing unit 52 and an edge surface 50*m* of the operating part body 50 facing the edge surface 52*m* is an inclined surface that spreads toward an outer surface side of the operating part body 50.

As described above, since an interval in a case where the edge surface 52*m* of the fixing unit 52 and the edge surface 50*m* of the operating part body 50 have most approached each other is the inclined surface that spreads toward the outer surface side of the operating part body 50, a trouble in which a finger is sandwiched between the edge surfaces of both members can be avoided in the forward and backward movement operation of the operating part body 50.

Figure 22:
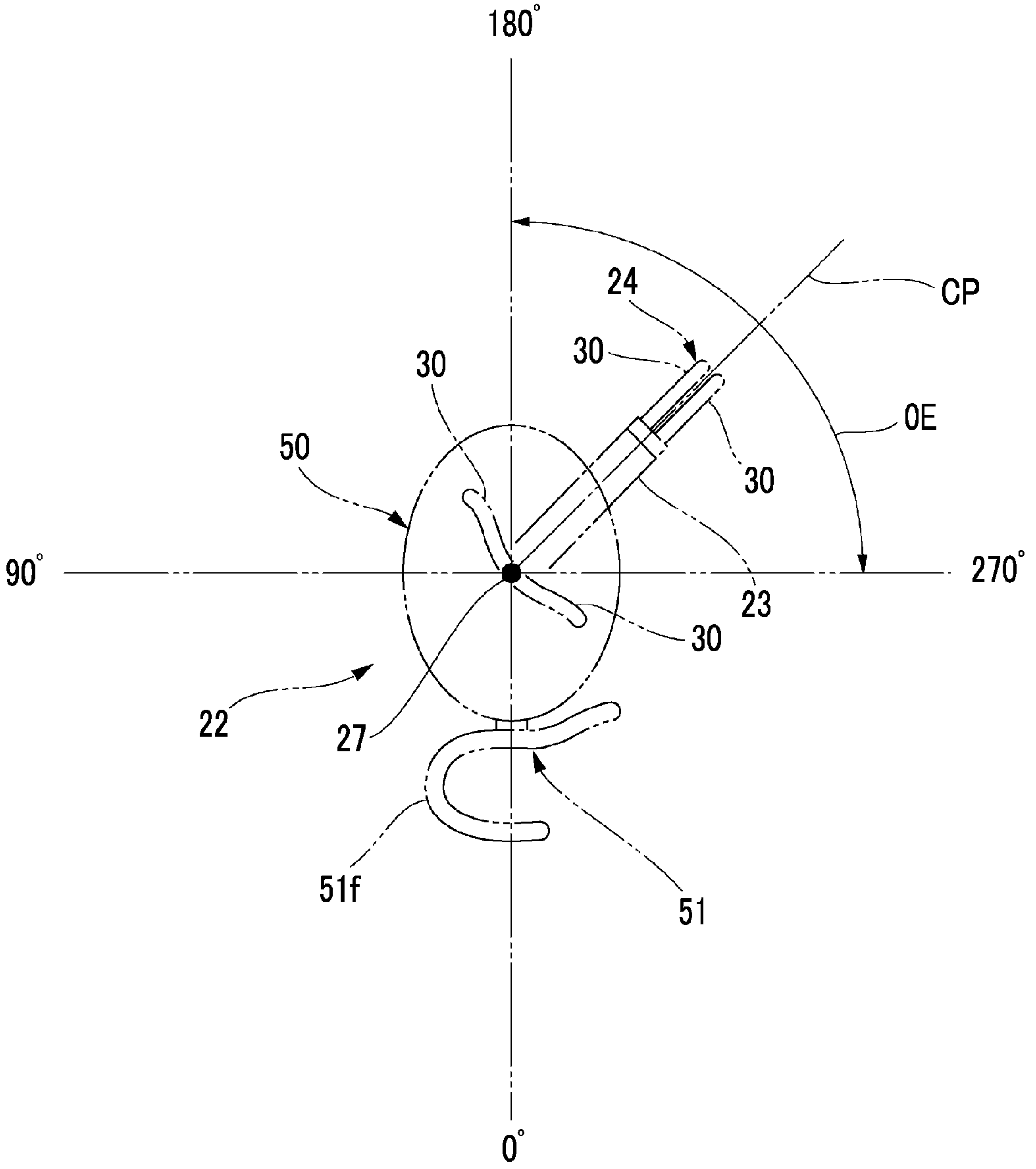
FIG. 22 is an explanatory schematic view for describing directions including an operation direction of an operation handle of the operating part and an operating direction of the grip part.

FIG. 22 is an explanatory schematic view for describing directions including an operation direction of the operation handle 51 of the operating part 22 and an operating direction of the grip part 24.

As shown in FIG. 22, in a case where the operation wire 27 is set linear and the operating part 22 is viewed along a direction of an axis of the operation wire 27 toward the distal end part 23 (in a case of being viewed from a direction of the operating part body 50 toward a distal end part 23 direction in FIG. 22), the position of a bending operation plane MS (see FIG. 23) of the bendable part 25 (the same position as the position of the distal end part 23 in FIG. 22) is positioned in a range OE that is larger than 180 degrees in a clockwise direction and that is smaller than 270 degrees in the clockwise direction in a circumferential direction of the axis (the axis shown by the operation wire 27 in FIG. 22) with a position where the operation handle 51 causing the operating part 22 to operate the bendable part 25 is provided (the position of 0 degree in FIG. 22) as a starting point.

In a case of being configured as described above, for example, in a case where the endoscope treatment tool 20 is attached to the endoscope operating part 7 and is used, in a relationship between an operation direction of the operator who operates the operation handle 51 (a linear direction indicating 0 degree in FIG. 22) and the bending operation plane MS of the bendable part 25 (including the distal end part 23) shown in the monitor 5, which is an endoscope screen, the position of the range OE less than 90 degrees in the circumferential direction is set to be above an upper side of the screen of the monitor 5 with an intermediate position CP (a position 225 degrees in the clockwise direction from the position of 0 degree) between a case where the upper side of the screen of the monitor 5 and an operation direction directly ahead of the operator (a linear direction indicating 180 degrees in FIG. 22) match each other and a case where the upper side of the screen of the monitor 5 and an operation direction that is 90 degrees to the right with respect to directly ahead of the operator (a linear direction indicating 270 degrees in FIG. 22) match each other as a center.

As described above, as the position of the bending operation plane MS of the bendable part 25 operated by the operating part 22 is positioned in the range OE that is larger than 180 degrees in the clockwise direction and that is less than 270 degrees clockwise with a position where the operation handle 51 is disposed as a starting point (0 degree), in a case of operating the operating part 22, the direction of the bending operation plane MS of the bendable part 25 and a direction of an operation screen are accepted to an operator's sense of operation without discomfort. As a result, the operability of the operating part 22 can be improved.

Figure 23:
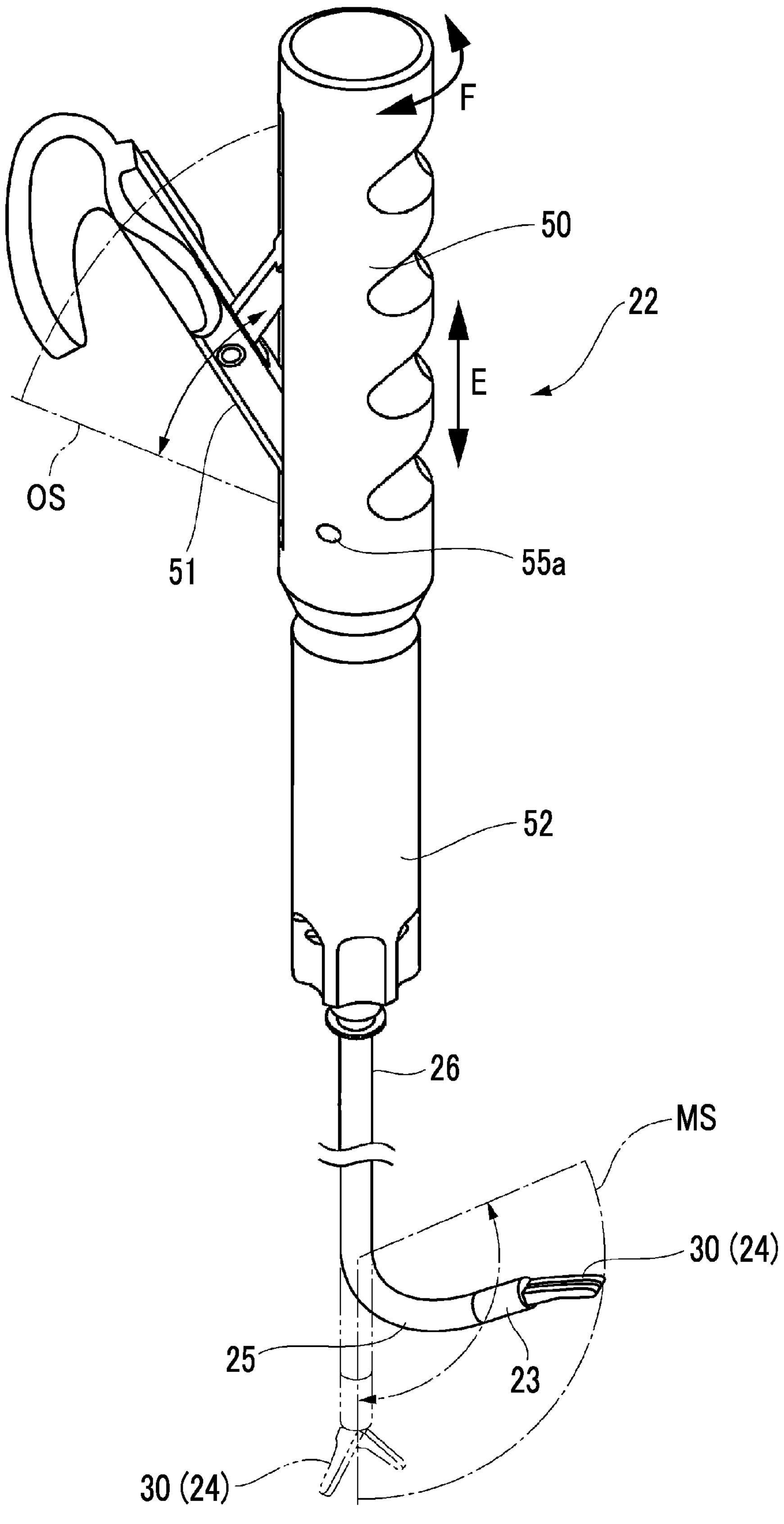
FIG. 23 is a perspective view for describing a relationship between an operation movement plane of the operation handle of the operating part and a bending operation plane of the bendable part.

FIG. 23 is a perspective view for describing a relationship between an operation movement plane OS of the operation handle 51 of the operating part 22 and the bending operation plane MS of the bendable part 25.

As shown in FIG. 23, the operation movement plane OS is an imaginary plane including a movement plane which is a fan-shaped movement plane drawn by the operation handle 51 of the operating part 22. In addition, the bending operation plane MS is an imaginary plane including a fan-shaped movement plane of the bendable part 25 that operates to be bent in a direction orthogonal to the imaginary plane where the grip claws 30 are opened and closed.

In addition, it is most preferable that the bending operation plane MS where the bendable part 25 operates to be bent with the pulling of the operation wire 27 is set at the position 225 degrees in the clockwise direction (the intermediate position CP in FIG. 22) with the operation movement plane OS in a case of operating the operation handle 51 as a starting point.

As described above, by setting the bending operation plane MS at the intermediate position CP 225 degrees in the clockwise direction with the operation movement plane OS in a case of operating the operation handle 51 as a starting point, an orientation in the middle of a fluctuation range where a manner of holding the operating part 22 is changed by the operator can be used in a relationship between an operation orientation of the operation handle 51 and a bending orientation of the bendable part 25. As a result, even in a case where the operator has changed the manner of holding (the operation orientation), discomfort caused by extreme fluctuations in an operating orientation of the bendable part 25 can be avoided, and endoscope procedures can be stabilized.

In addition, the operating part 22 has the operating part body 50 that moves rotationally with respect to the fixing unit 52 attaching the operating part to a predetermined part and that is capable of rotationally moving an orientation of the distal end part 23 and the operation handle 51 that moves the operation wire 27 through opening and closing with a rotational movement fulcrum with respect to the operating part body 50 as a center.

As described above, since the operating part 22 is rotatable with respect to the fixing unit 52, the distal end part 23 can be rotated by the operating part body 50, and the operation handle 51 can be opened and closed with the rotational movement fulcrum (the rotational movement support shaft part 55*a*) with respect to the operating part body 50 as a center. Thus, the rotational movement of the operating part body 50 and the opening and closing of the operation handle 51 can be easily performed.

Figure 24:
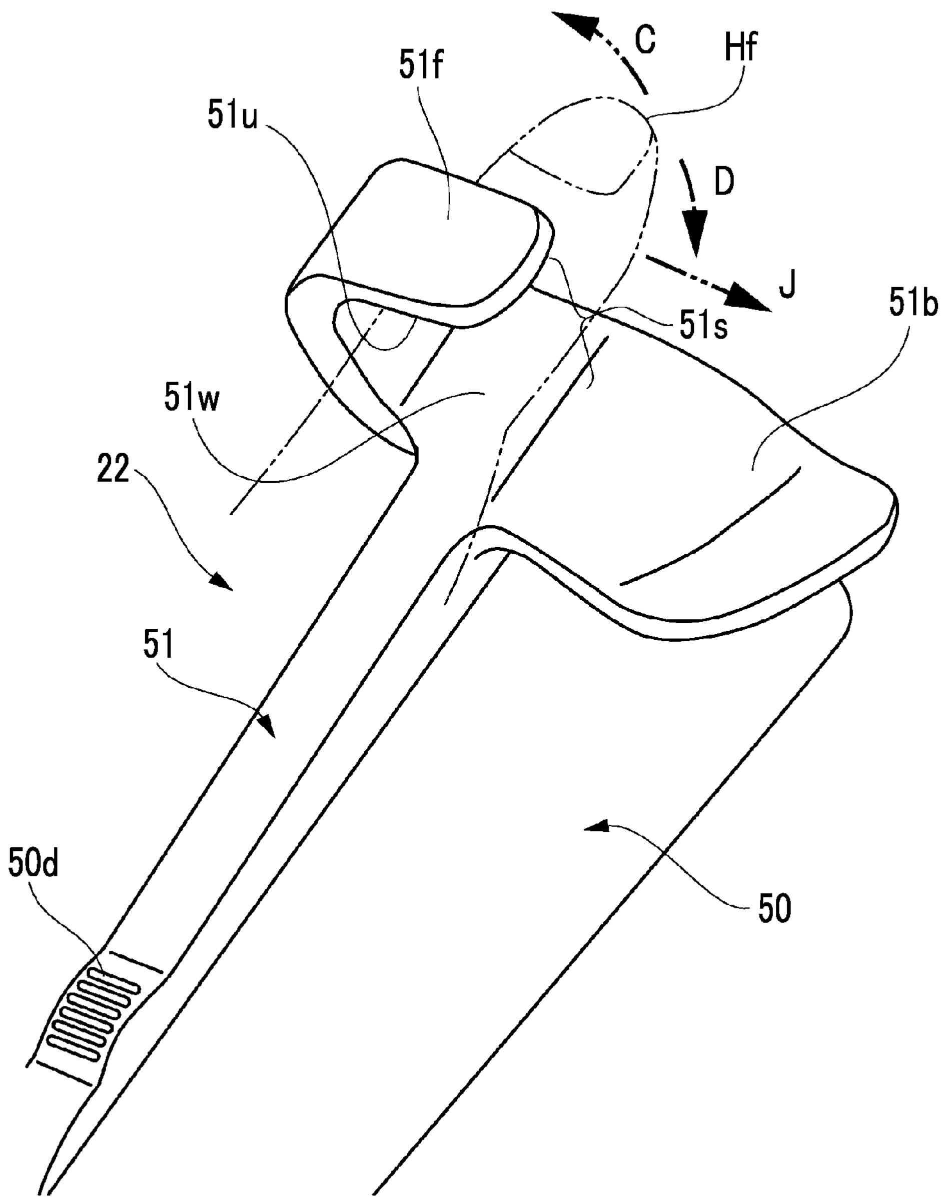
FIG. 24 is an enlarged perspective view in which an operation handle in the endoscope treatment tool shown in FIG. 23 is viewed from above.

FIG. 24 is an enlarged perspective view in which the operation handle 51 in the endoscope treatment tool 20 is viewed from above. As shown in FIG. 24, the operation handle 51 has a first protruding portion 51*f*, in which at least a side surface 51*w* on a side where the operation handle 51 is closed and a side surface 51*u* on a side where the operation handle 51 is opened are bent to be capable of simultaneously facing a finger Hf that operates the operation handle 51.

As described above, as the operation handle 51 is provided with the first protruding portion 51*f*, the side surfaces 51*u* and 51*w* are disposed on the inside and outside of the finger Hf with respect to the finger Hf that operates the operation handle 51. Thus, the operation handle 51 can be freely opened and closed by moving the finger Hf placed on the inside of the first protruding portion 51*f* in a closing direction (the arrow D direction) or an opening direction (the arrow C direction).

In addition, the first protruding portion 51*f* has a hook shape having an open part 51*s* of which at least one side (a right side in FIG. 24) in a direction orthogonal to the opening and closing direction of the operation handle 51 is opened.

As described above, due to the hook shape of which the one side in the direction orthogonal to the opening and closing direction of the operation handle 51 is the open part 51*s*, for example, the finger Hf that operates the operation handle 51 can be slidingly moved from the operation handle 51 in an orthogonal horizontal direction (the arrow J direction).

The operation handle 51 has a second protruding portion 51*b* that protrudes in a direction orthogonal to the opening and closing direction of the operation handle 51.

As described above, since the second protruding portion 51*b* which protrudes in the direction orthogonal to the opening and closing direction of the operation handle 51 is included, the finger can be hooked to the operation handle 51 even in a case where the finger is shifted in the horizontal direction with respect to the operation handle 51. As a result, even in a case where the manner of holding the operating part 22 with respect to a hand changes in a circumferential direction of the operating part 22, an operation of the operation handle 51 is possible with the second protruding portion 51*b*. For example, in a case where the finger Hf is a finger of the right hand and the right hand is twisted to be rotated in the arrow C direction, an operation of the first protruding portion 51*f* by the finger Hf is difficult. However, the operation of the operation handle 51 can be easily performed by moving the finger Hf in the second protruding portion 51*b* from the first protruding portion 51*f* and performing an operation of the second protruding portion 51*b* with the finger Hf.

In addition, the first protruding portion 51*f* and the second protruding portion 51*b* are continuously formed. Accordingly, an operable surface of the operation handle 51 widens as a continuous surface, an operable range widens even in a case where a rotation operation is performed with an opening and closing operation of the operation handle 51, and the rotation operation and the opening and closing operation can be performed without separating the finger Hf from the operation handle 51.

Figure 25:
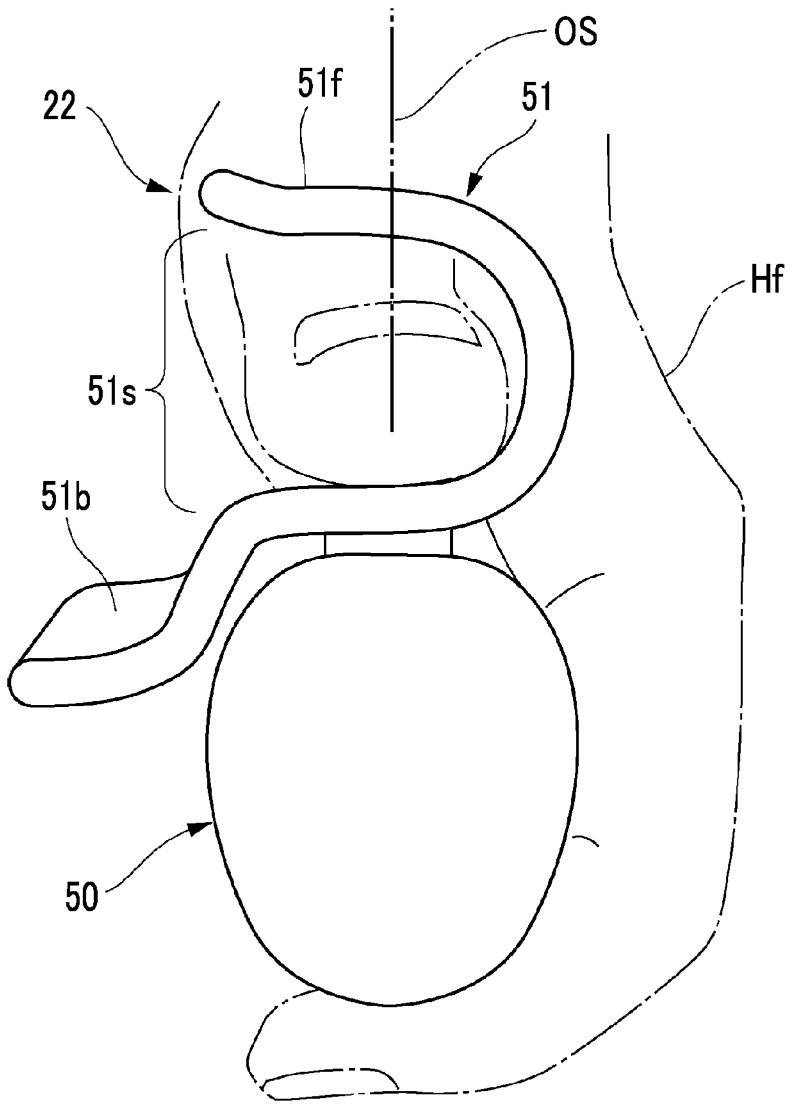
FIG. 25 is a view of the operating part body in the endoscope treatment tool shown in FIG. 23, which is viewed from a distal end side of an axial direction thereof.

FIG. 25 is a view of the operating part body 50 in the endoscope treatment tool 20 viewed from a distal end side in an axial direction thereof. As shown in FIG. 25, the operating part 22 has a longitudinal direction and a lateral direction in a horizontal cross section in which the operating part body 50 is orthogonal to an axial direction of the operating part 22. In addition, the longitudinal direction is substantially parallel to a plane including the operation movement plane OS of the operation handle 51.

As described above, since the longitudinal direction is substantially parallel to the plane including the operation movement plane OS of the operation handle 51 in the horizontal cross section orthogonal to the axial direction of the operating part 22, as shown in FIG. 25, in a case of holding the operating part 22 with a hand, the finger Hf hooked to the operation handle 51 and the palm of the hand holding the operating part body 50 fit well, and thereby the operating part 22 is excellent in operability. In addition, even in a case where the operator does not view the operation handle 51, the direction of the operation handle 51 can be easily determined as the operator grips the operation handle 51.

FIGS. 26 to 31 show a treatment method for ESD as an example of a treatment method using the endoscope treatment tool 20. The operation wire 27 is pulled to the operating part 22 side in response to the swinging of the operation handle 51 in the closing direction D. In addition, an endoscope treatment tool used in combination with the endoscope treatment tool 20 is an incision tool and is a high-frequency forcep 60 having a pair of openable and closable claws 61 at a distal end part thereof (see FIG. 29). The pair of claws 61 are opened and closed by an operating part of the high-frequency forcep 60. In a state where the pair of claws 61 are closed and a living body tissue is gripped by the pair of claws 61, a high-frequency current flows between the pair of claws 61 and a return electrode plate via the living body tissue, or a high-frequency current flows between the pair of claws 61. Consequently, the living body tissue is cauterized, and incision is performed.

Figure 26:
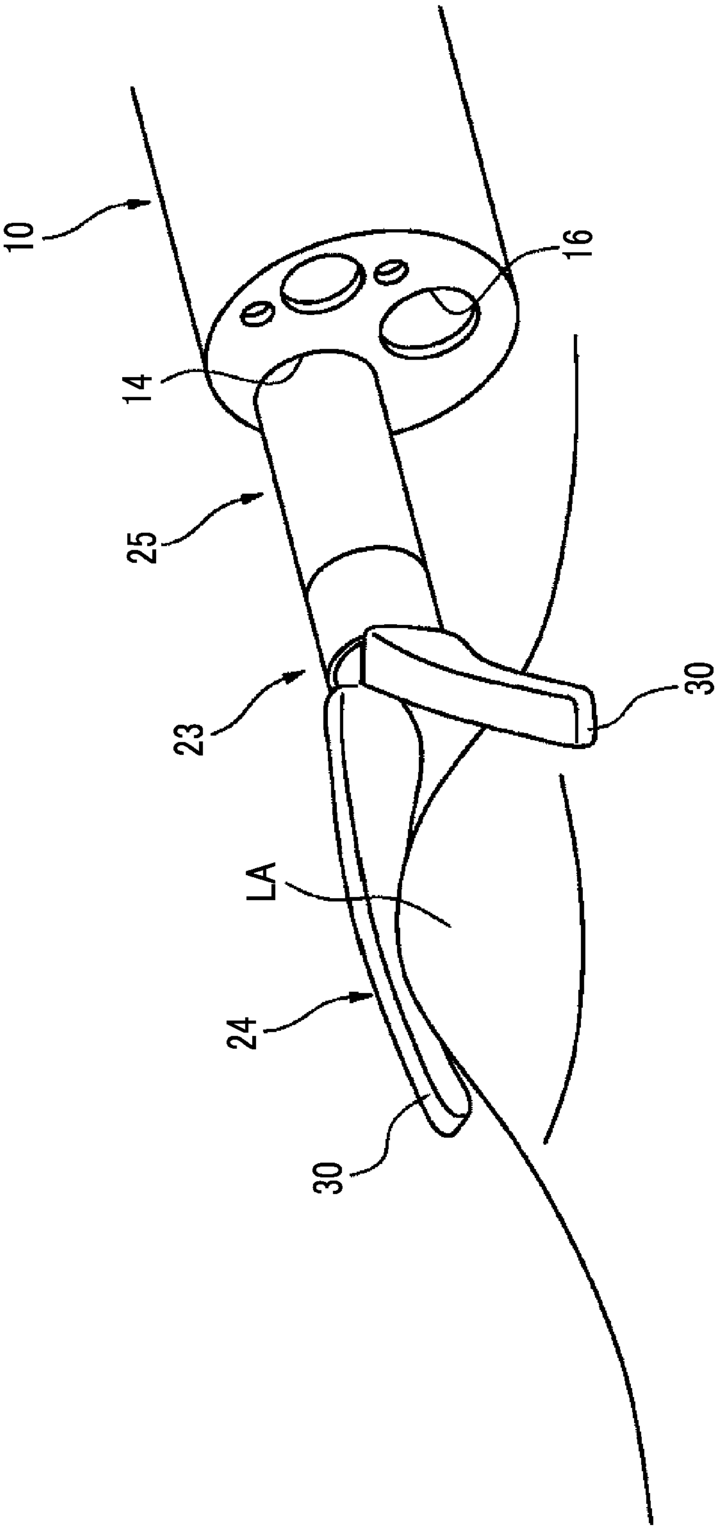
FIG. 26 is a view showing an example of a treatment method using the endoscope treatment tool of FIG. 2.

As shown in FIG. 26, the endoscope 2 is inserted into the body, and the endoscope distal end part 10 is disposed at the side of a lesion part LA of a mucous membrane layer. The endoscope treatment tool 20 is inserted into the first treatment tool channel 14 of the endoscope 2, and the distal end part 23 and the bendable part 25 of the endoscope treatment tool 20 protrude from the edge surface of the endoscope distal end part 10. Then, the lesion part LA is gripped by the grip part 24 of the distal end part 23 through the operation of the operating part 22 of the endoscope treatment tool 20.

In a case where the lesion part LA is gripped by the grip part 24, first, the operation handle 51 (see FIG. 10) of the operating part 22 is operated in the opening direction C. As shown in 26, the operation wire 27 is pushed out to the distal end part 23 side in response to the operation of the operation handle 51. As the operation wire 27 is pushed out, the bendable part 25 is linearly extended and is laid along the longitudinal axis of the connecting part 26. In addition, as the operation wire 27 is pushed out, the pair of grip claws 30 of the grip part 24 are opened. Then, the operating part body 50 is pushed and pulled as appropriate, and the lesion part LA is disposed between the pair of grip claws 30.

Figure 27:
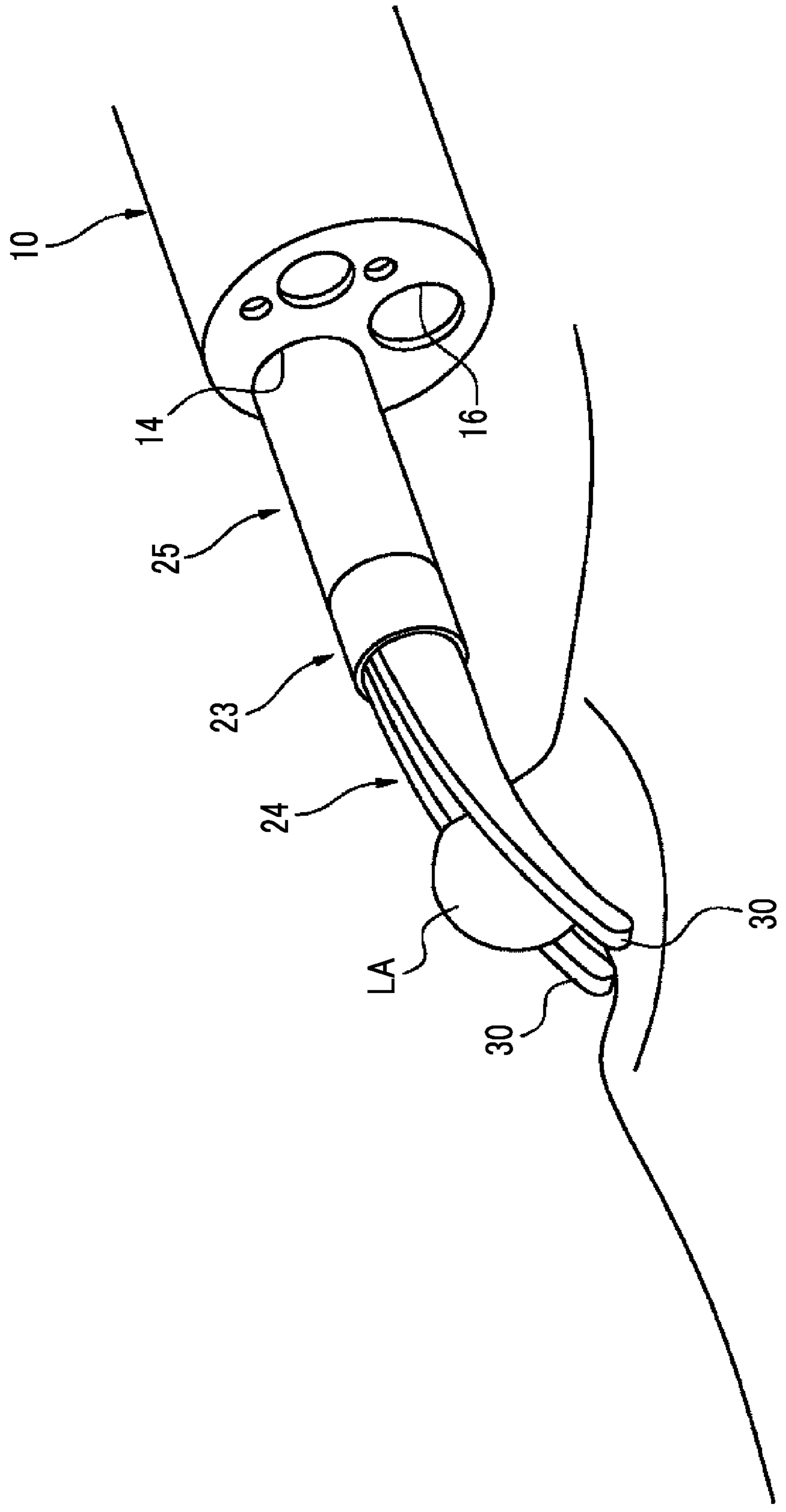
FIG. 27 is a view showing an example of the treatment method using the endoscope treatment tool of FIG. 2.
Figure 28:
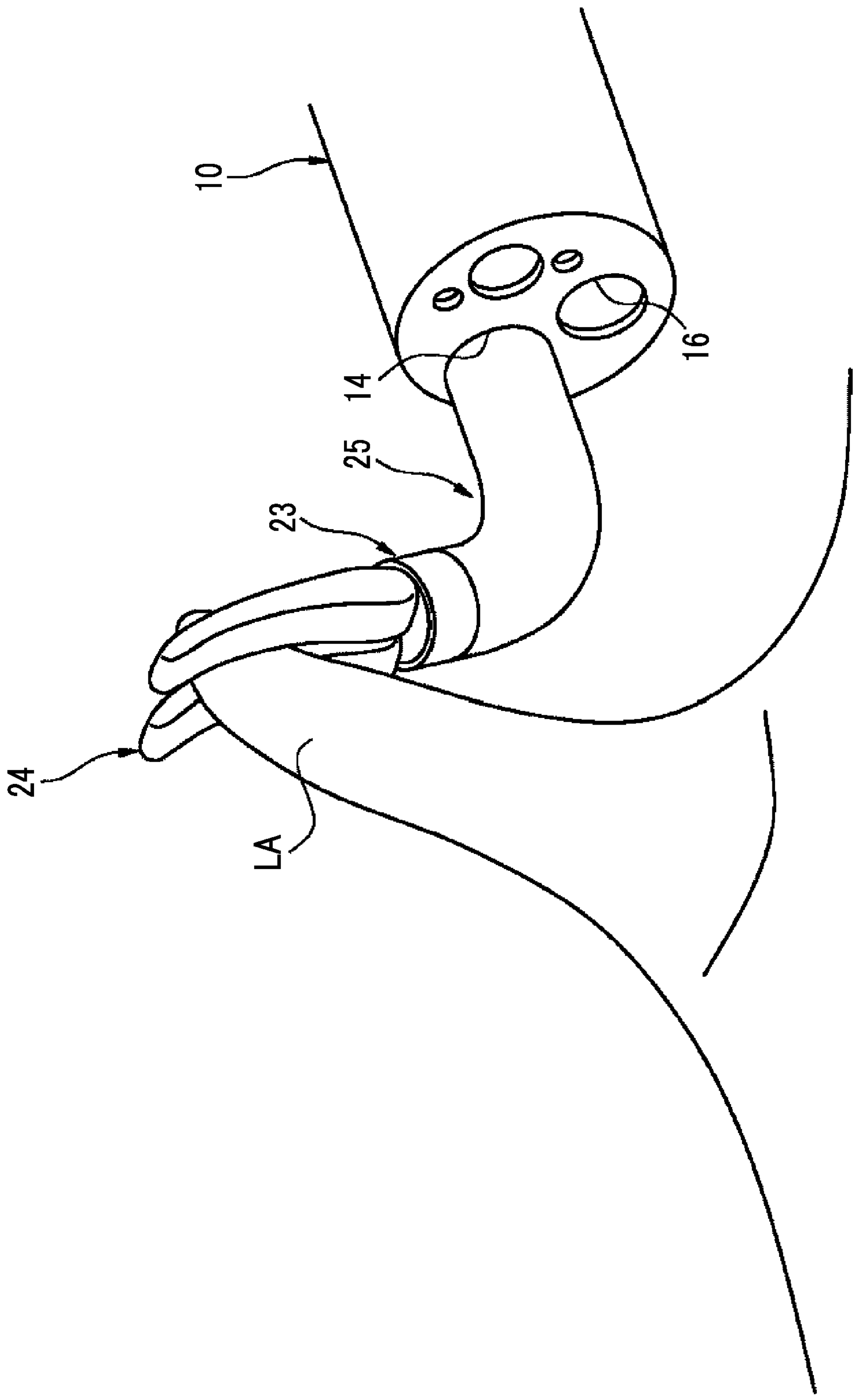
FIG. 28 is a view showing an example of the treatment method using the endoscope treatment tool of FIG. 2.

The operation handle 51 is operated in the closing direction D in a state where the lesion part LA is disposed between the pair of grip claws 30. Accordingly, the operation wire 27 is pulled to the operating part 22 side. As the operation wire 27 is pulled, the pair of grip claws 30 are closed first and the lesion part LA is gripped by the grip part 24 as shown in FIG. 27. Then, after the lesion part LA is gripped by the grip part 24, the bendable part 25 is bent as shown in FIG. 28. Accordingly, the grip part 24 is erected from a state of being laid along the longitudinal axis of the connecting part 26, and the lesion part LA gripped by the grip part 24 is lifted.

Figure 29:
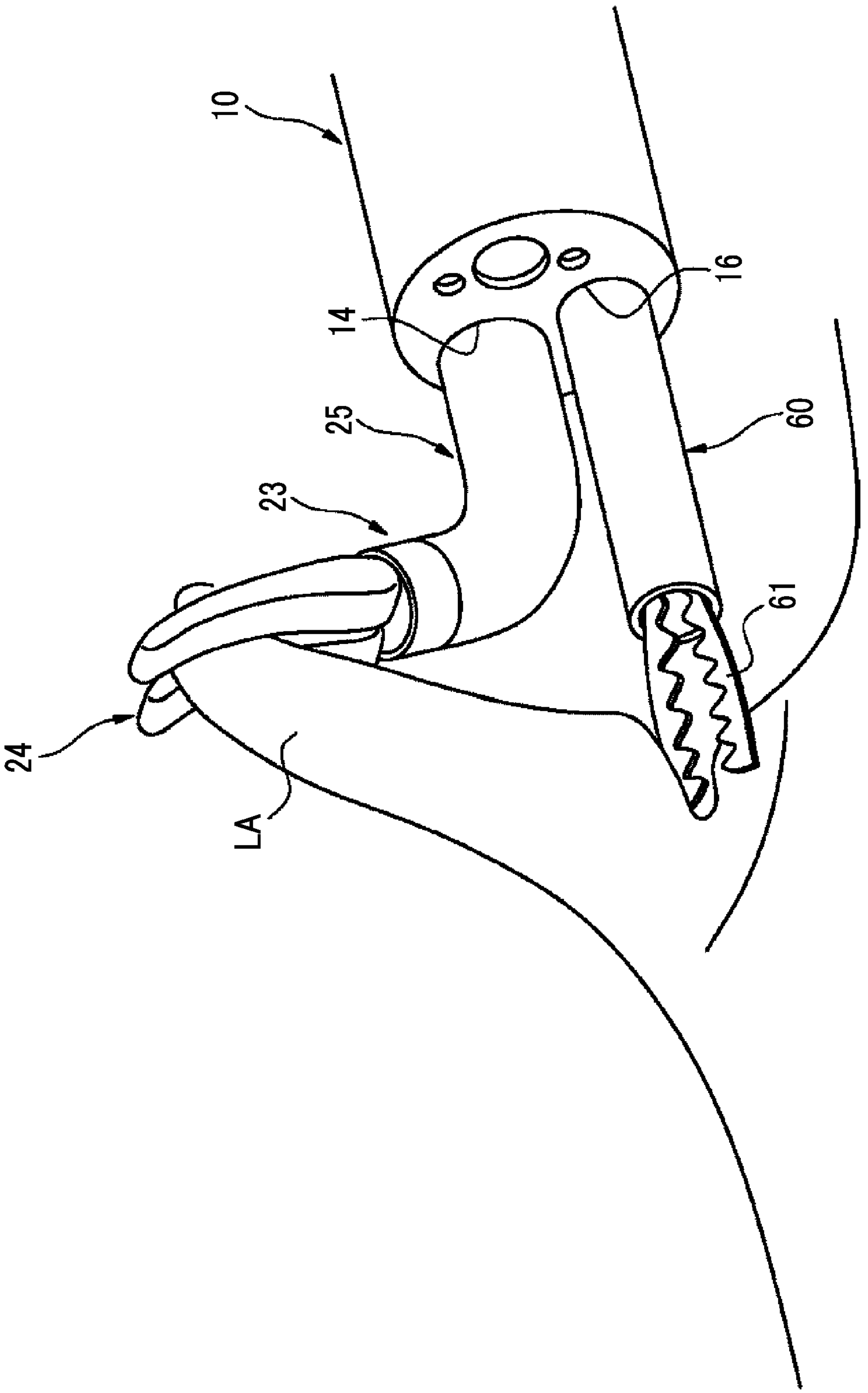
FIG. 29 is a view showing an example of a treatment method using a combination of the endoscope treatment tool of FIG. 2 and another endoscope treatment tool.

In a state where the lesion part LA is being lifted, the high-frequency forcep 60 inserted into the second treatment tool channel 16 of the endoscope 2 protrudes from the edge surface of the endoscope distal end part 10 as shown in FIG. 29. The pair of claws 61 of the high-frequency forcep 60 are disposed at a lower part of the lesion part LA, and the lower part of the lesion part LA is incised by the pair of claws 61. As the incision proceeds, the lifted lesion part LA may be released once, re-gripped, and then lifted. In a case where the lesion part LA that has been once incised is lifted, the lower part is exposed so that the lower part is easily visible. Therefore, excision can be performed safely, reliably, and easily. The incision proceeds as the high-frequency forcep 60 is pushed and pulled as appropriate, and the lesion part LA including a submucosal layer is gradually peeled off.

Since the lesion part LA can be gripped from the side of the lesion part LA and the gripped lesion part LA can be lifted only through the operation of the operation handle 51 of the endoscope treatment tool 20 as described above, the operation is simple. Accordingly, lifting of the lesion part LA, exposing the lower part of the lesion part LA so as to be easily visible by lifting the lesion part LA, and accordingly treatment for the lower part of the lifted lesion part LA can be performed safely, reliably, and easily. Further, in the present example, the operation state of the operation handle 51 can be maintained by the friction adjusting mechanisms 70 and 73. Therefore, even after the hand of the operator is separated from the operation handle 51, the lesion part LA can be maintained in a lifted state. Accordingly, the operator can concentrate on the operation of the high-frequency forcep 60 in a case of incision, and by further simplifying the operation, the treatment for the lower part of the lesion part LA can be performed more easily.

In a case of incision, the operating part body 50 of the operating part 22 may be pushed and pulled in the arrow E direction of FIG. 10 and/or the operating part body 50 may be rotated in the arrow F direction of FIG. 10. As described above, the connecting part 26 has stiffness that allows translational and rotational power to be transmitted from the operating part 22 side to the bendable part 25 side, and pushing, pulling, and rotation of the operating part body 50 are transmitted to the bendable part 25 via the connecting part 26.

Figure 30:
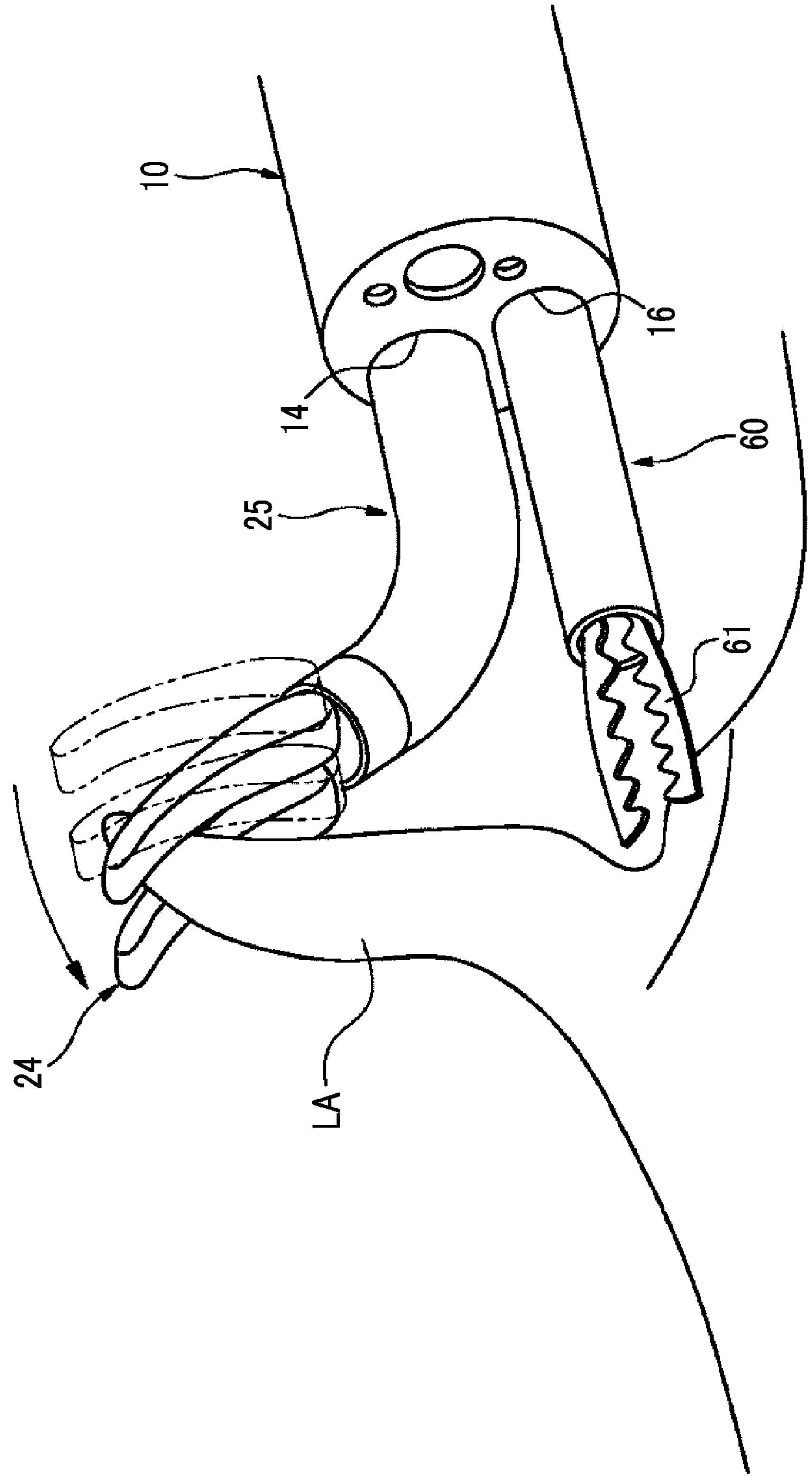
FIG. 30 is a view showing an example of the treatment method using the combination of the endoscope treatment tool of FIG. 2 and the other endoscope treatment tool.

FIG. 30 shows a case where the operating part body 50 is rotated. The connecting part 26 is rotated about the longitudinal axis of the connecting part 26 in response to the rotation of the operating part body 50. In a state where the bendable part 25 is bent, the grip part 24 is rotated while maintaining an erected state with respect to the longitudinal axis of the connecting part 26, and the lesion part LA gripped by the grip part 24 swings about the longitudinal axis of the connecting part 26.

Figure 31:
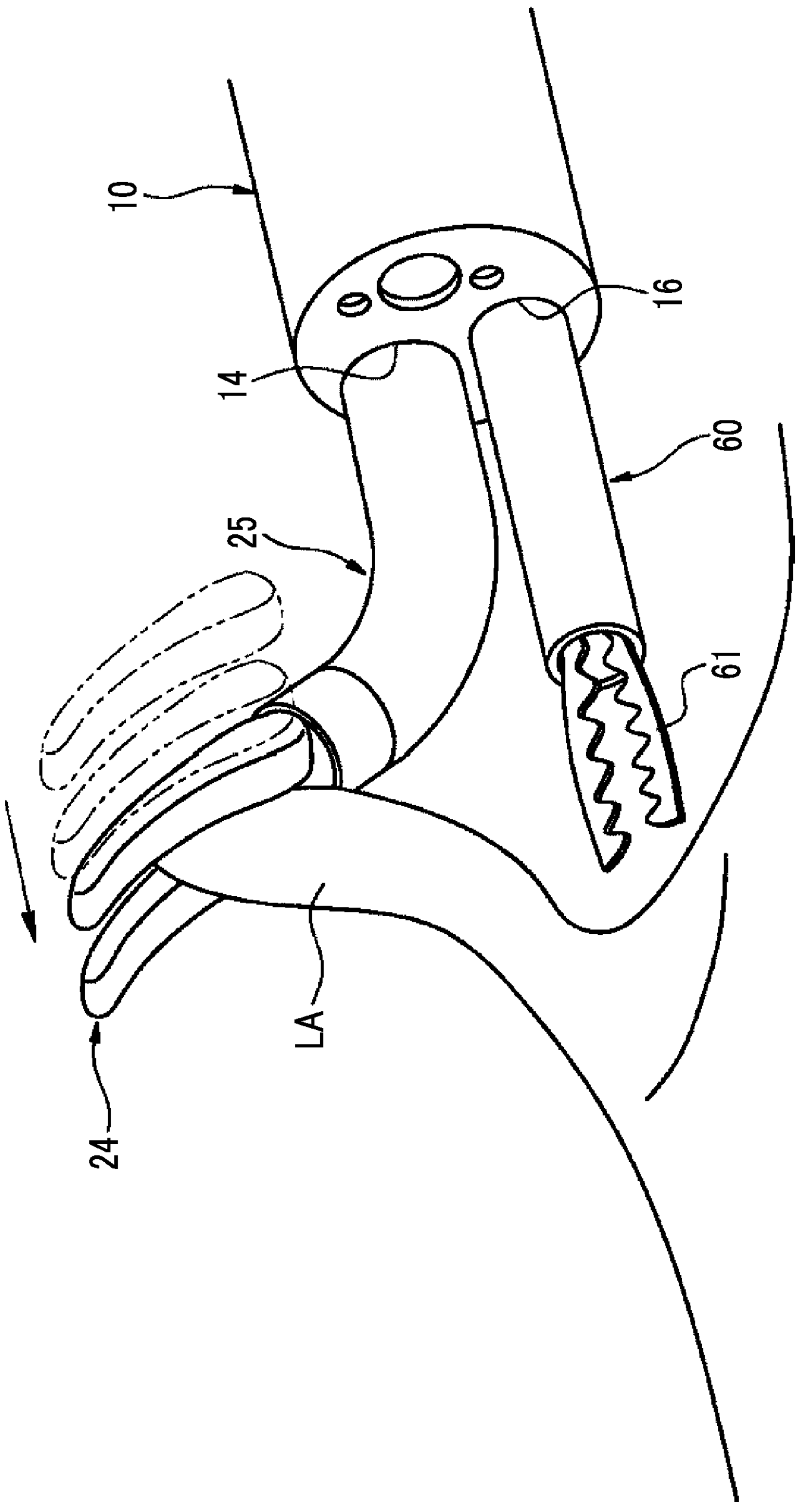
FIG. 31 is a view showing an example of the treatment method using the combination of the endoscope treatment tool of FIG. 2 and the other endoscope treatment tool.

FIG. 31 shows a case where the operating part body 50 is pushed and pulled. The connecting part 26 is moved forward and backward in an axial direction, which is the longitudinal axis of the connecting part 26, in response to the pushing and pulling of the operating part body 50. In a state where the bendable part 25 is bent, the grip part 24 is moved forward and backward while maintaining an erected state with respect to the longitudinal axis of the connecting part 26, and the lesion part LA gripped by the grip part 24 is pushed and pulled in the axial direction, which is the longitudinal axis of the connecting part 26.

By swinging and/or pushing and pulling the lesion part LA as appropriate, for example, an incised wound can be widened. Accordingly, treatment for the lower part of the lesion part LA can be performed more easily. Thus, as the operation state of the operating part body 50 is maintained by the friction mechanism 80, the incised wound can be maintained in a widened state even after the hand of the operator is separated from the operating part body 50. Accordingly, treatment for the lower part of the lesion part LA can be performed more easily.

Although the embodiment of the present invention has been described hereinbefore, the present invention is not limited to the embodiment and can be subjected to modification, improvement, or the like as appropriate.

For example, although the link member 57 is sandwiched between the pair of wire holding parts 56 to have a structure, in which there are two pairs of cam surfaces, in the friction adjusting mechanism 70 according to the embodiment, without being limited thereto, for example, facing cam surfaces may be a pair.

In addition, although an O-ring is used as the elastic member 73*o* in the slide-type friction adjusting mechanism 73 of the embodiment, the O-ring may not be used.

In addition, although a configuration where four protrusions 52*d* are provided is adopted in the friction mechanism 80 of the embodiment, without being limited to four, a larger number or a smaller number of protrusions may be provided.

In addition, although the concave part 50*c* and the convex part 50*d* that can be engaged with fingers are provided in the friction mechanism 80 of the embodiment, both of the concave part 50*c* and the convex part 50*d* may not be provided, or at least one of them may be provided.

Figure 32:
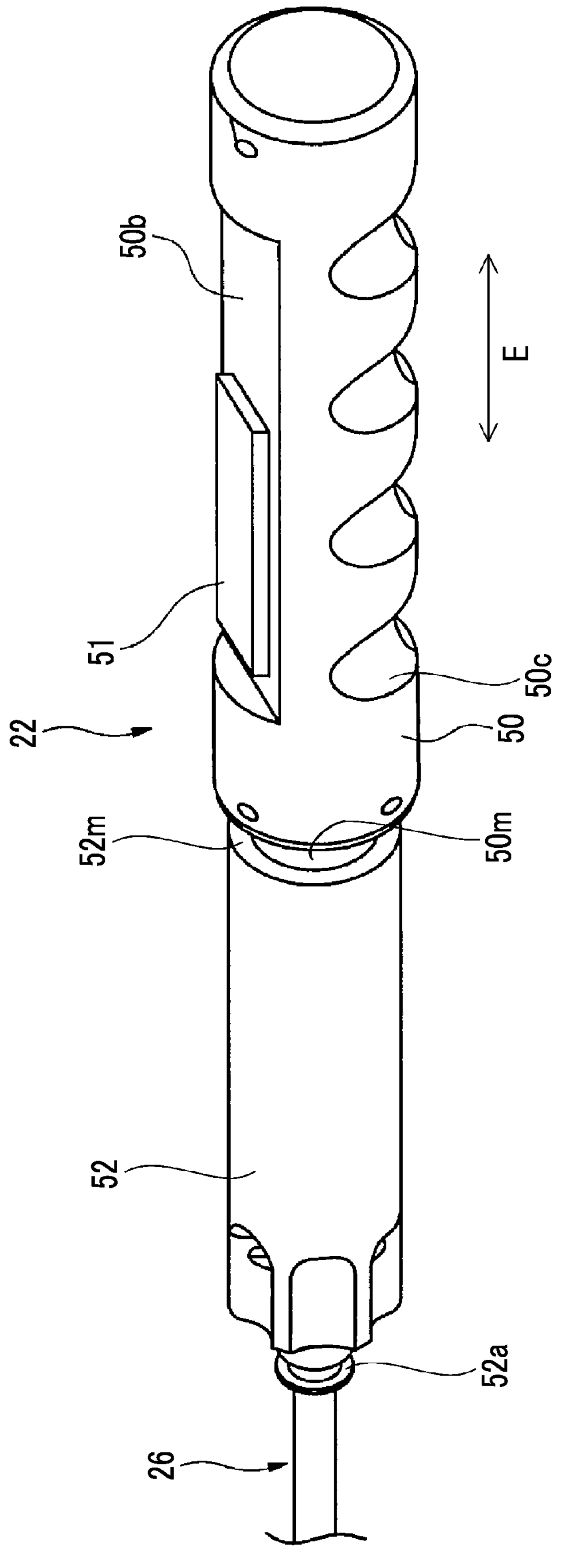
FIG. 32 is a view showing another configuration example of the operating part of FIG. 10.

In addition, although a configuration where the operation handle 51 in the operating part 22 of the embodiment is swingably provided to overhang from the operating part body 50 and the wire holding part 56 is moved through the swinging has been described, the present invention is not limited to such a configuration. For example, as shown in FIG. 32, the operation handle 51 may be a member that is provided on a plane portion 50*b* provided at the operating part body 50 and that is movable in the arrow E-direction along the plane portion 50*b*. The operation handle 51 is operated, for example, by the thumb of the operator gripping the operating part body 50.

In this case, the operation handle 51 is coupled to the wire holding part 56. In a case where the operation handle 51 is moved to the distal end side of the operating part body 50 (an upper side of FIG. 32), the wire holding part 56 also moves to the distal end side of the operating part body 50, and the operation wire 27 is pulled. In addition, in a case where the operation handle 51 is moved to a proximal end side (a lower side of FIG. 32) of the operating part body 50, the wire holding part 56 also moves to the proximal end side of the operating part body 50, and the operation wire 27 is loosened. That is, in the configuration shown in FIG. 32, through an operation of moving the operation handle 51 up and down, the same operation as an operation of swinging the operation handle 51 shown in FIG. 11 or the like can be realized.

The positions and shapes of the operation handle 51 and the plane portion 50*b* in the configuration shown in FIG. 32 are not limited to the configuration shown in FIG. 32. For example, the plane portion 50*b* may be positioned closer to the distal end side of the operating part body 50 than the example shown in FIG. 32.

At least the following matters are described in the present specification.

(1)

An endoscope treatment tool comprising:
- a distal end part that is provided with an openable and closable grip part;
- a bendable part that is provided to be adjacent to the distal end part and that is bendable;
- an operating part into which an operation of closing the grip part and an operation of bending the bendable part are input; and
- an operation wire that transmits the operations at the operating part respectively to the grip part and the bendable part,
- wherein the operating part includes
  - an operating part body that movably holds a wire holding part to which the operation wire is connected, and
  - an operation handle that moves the wire holding part, and
  - has a friction adjusting mechanism that increases a frictional force for locking the wire holding part to correspond to an increase in a pulled amount of the operation wire which is caused by the wire holding part interlocked with an operation of the operation handle.

(2)

The endoscope treatment tool according to (1),
wherein the operation handle is swingably provided to overhang from the operating part body and moves the wire holding part through swinging.

(3)

The endoscope treatment tool according to (1) or (2),
wherein the operation handle is coupled to the wire holding part to be slidably movable via a link member.

(4)

The endoscope treatment tool according to any one of (1) to (3),
wherein the friction adjusting mechanism is provided at a rotational movement support shaft part that supports the operation handle to be movable rotationally, and
the rotational movement support shaft part comprises a cam part that is capable of changing a contact pressure to correspond to a rotation angle about a shaft of the rotational movement support shaft part.

(5)

The endoscope treatment tool according to (4),
wherein the cam part is provided at the wire holding part in the operating part body.

(6)

The endoscope treatment tool according to (5),
wherein the rotational movement support shaft part is provided with a fastening member that penetrates the rotational movement support shaft part, and a fastening force of the rotational movement support shaft part is configured to be adjustable.

(7)

The endoscope treatment tool according to any one of (1) to (3),
wherein the friction adjusting mechanism includes
- the wire holding part that slidingly moves with respect to the operating part body, and a sliding portion that is slidingly contactable with the wire holding part by a movement of the wire holding part, and at least a part of the sliding portion has an inclined structure that increases a contact pressure on the wire holding part to correspond to the increase in the pulled amount of the operation wire.

(8)

The endoscope treatment tool according to (7), wherein the sliding portion includes a first sliding portion, of which the contact pressure with respect to the wire holding part is substantially constant, and a second sliding portion having the inclined structure, of which the contact pressure with respect to the wire holding part increases to correspond to the increase in the pulled amount of the operation wire.

(9)

The endoscope treatment tool according to (8), wherein the first sliding portion is set to have a frictional force smaller than a frictional force of the second sliding portion.

(10)

The endoscope treatment tool according to (8) or (9), wherein the second sliding portion has a piston that is provided at one end part of the wire holding part, a cylinder that movably accommodates the piston in an axial direction of the piston, and a ring-shaped elastic member that is provided on an outer periphery of the piston and that is in contact with an inner wall surface of the cylinder.

(11)

The endoscope treatment tool according to (10), wherein the ring-shaped elastic member is an O-ring.

(12)

The endoscope treatment tool according to any one of (1) to (11), wherein as a movement amount by which the operation wire is pulled increases, a force pulling in a direction of restoring the operation wire increases.

(13)

The endoscope treatment tool according to (12), wherein the bendable part that is bent by pulling of the operation wire has an elastic force in a direction returning from a bent state to a linear state.

(14)

The endoscope treatment tool according to (13), wherein an outer coat of the bendable part is made of an elastic member.

(15)

The endoscope treatment tool according to (13) or (14), wherein a member inside an outer coat of the bendable part is made of an elastic material.

(16)

An endoscope device comprising:

a first treatment tool that is the endoscope treatment tool according to any one of (1) to (15);

a second treatment tool; and an endoscope that has a first treatment tool channel into which the first treatment tool is insertable and a second treatment tool channel into which the second treatment tool is insertable.

(17)

A treatment method comprising:

by using the endoscope device according to (16), disposing the distal end part of the first treatment tool at a lesion part in a body through the first treatment tool channel of the endoscope;

gripping the lesion part with the grip part of the first treatment tool;

lifting, in a state where the lesion part is gripped, the lesion part by bending the bendable part of the first treatment tool; and treating, in a state where the lesion part is lifted, a lower part of the lesion part with the second treatment tool inserted into the second treatment tool channel of the endoscope.

Although various types of embodiments have been described hereinbefore with reference to the drawings, it is evident that the present invention is not limited to such examples. It is clear that those skilled in the art can come up with various types of changed examples or modified examples within the scope of claims, and it is understood that those examples obviously belong to the technical scope of the present invention. In addition, without departing from the gist of the invention, each of components in the embodiments may be combined in any manner.

The present application is based on the U.S. provisional application filed on Nov. 30, 2020 (63/118,974), the content of which is incorporated herein by reference.

EXPLANATION OF REFERENCES

20: endoscope treatment tool
22: operating part
23: distal end part
25: bendable part
26: connecting part
27: operation wire
50: operating part body
51: operation handle
52: fixing unit
52*d*: protrusion
55: rotational movement support shaft part
56: wire holding part
57: link member
58*m*: fastening member
59: friction member
70, 73: friction adjusting mechanism
71: first sliding portion (sliding portion)
72: second sliding portion (sliding portion)
73*c*: cylinder
73*o*: elastic member
73*p*: piston
75: slide ring
76: friction member
77: O-ring
80: friction mechanism
81: first friction part
82: second friction part
MS: bending operation plane
OS: operation movement plane

What is claimed is:

1. An endoscope treatment tool comprising:

a distal end part that is provided with an openable and closable grip part;

a bendable part that is provided to be adjacent to the distal end part and that is bendable;

an operating part into which an operation of closing the grip part and an operation of bending the bendable part are input; and an operation wire that transmits the operations at the operating part respectively to the grip part and the bendable part, wherein the operating part includes an operating part body that movably holds a wire holding part to which the operation wire is connected, and an operation handle that moves the wire holding part, and has a friction adjusting mechanism that increases a frictional force for locking the wire holding part to correspond to an increase in a pulled amount of the operation wire which is caused by the wire holding part interlocked with an operation of the operation handle, wherein the bendable part includes a plurality of bending pieces and an outer coat, wherein the friction adjusting mechanism is provided at a rotational movement support shaft part that supports the operation handle to be movable rotationally, and the rotational movement support shaft part comprises a cam part that is capable of changing a contact pressure to correspond to a rotation angle about a shaft of the rotational movement support shaft part, wherein the cam part is provided at the wire holding part in the operating part body, wherein the rotational movement support shaft part is provided with a fastening member that penetrates the rotational movement support shaft part, and a fastening force of the rotational movement support shaft part is configured to be adjustable.

2. The endoscope treatment tool according to claim 1, wherein the operation handle is swingably provided to overhang from the operating part body and moves the wire holding part through swinging.

3. The endoscope treatment tool according to claim 1, wherein the operation handle is coupled to the wire holding part to be slidably movable via a link member.

4. The endoscope treatment tool according to claim 1, wherein as a movement amount by which the operation wire is pulled increases, a force pulling in a direction of restoring the operation wire increases.

5. The endoscope treatment tool according to claim 4, wherein the bendable part that is bent by pulling of the operation wire has an elastic force in a direction returning from a bent state to a linear state.

6. The endoscope treatment tool according to claim 5, wherein an outer coat of the bendable part is made of an elastic member.

7. The endoscope treatment tool according to claim 5, wherein a member inside an outer coat of the bendable part is made of an elastic material.

8. An endoscope device comprising:

a first treatment tool that is the endoscope treatment tool according to claim 1;

a second treatment tool; and an endoscope that has a first treatment tool channel into which the first treatment tool is insertable and a second treatment tool channel into which the second treatment tool is insertable.

9. A treatment method comprising:

by using the endoscope device according to claim 8, disposing the distal end part of the first treatment tool at a lesion part in a body through the first treatment tool channel of the endoscope;

gripping the lesion part with the grip part of the first treatment tool;

lifting, in a state where the lesion part is gripped, the lesion part by bending the bendable part of the first treatment tool; and treating, in a state where the lesion part is lifted, a lower part of the lesion part with the second treatment tool inserted into the second treatment tool channel of the endoscope.

10. An endoscope treatment tool comprising:

a distal end part that is provided with an openable and closable grip part;

a bendable part that is provided to be adjacent to the distal end part and that is bendable;

an operating part into which an operation of closing the grip part and an operation of bending the bendable part are input; and an operation wire that transmits the operations at the operating part respectively to the grip part and the bendable part, wherein the operating part includes an operating part body that movably holds a wire holding part to which the operation wire is connected, and an operation handle that moves the wire holding part, and has a friction adjusting mechanism that increases a frictional force for locking the wire holding part to correspond to an increase in a pulled amount of the operation wire which is caused by the wire holding part interlocked with an operation of the operation handle, wherein the bendable part includes a plurality of bending pieces and an outer coat, wherein the friction adjusting mechanism includes the wire holding part that slidingly moves with respect to the operating part body, and a sliding portion that is slidingly contactable with the wire holding part by a movement of the wire holding part, and at least a part of the sliding portion has an inclined structure that increases a contact pressure on the wire holding part to correspond to an increase in the pulled amount of the operation wire, wherein the sliding portion includes a first sliding portion, of which the contact pressure with respect to the wire holding part is substantially constant, and a second sliding portion having the inclined structure, of which the contact pressure with respect to the wire holding part increases to correspond to the increase in the pulled amount of the operation wire.

11. The endoscope treatment tool according to claim 10, wherein the first sliding portion is set to have a frictional force smaller than a frictional force of the second sliding portion.

12. The endoscope treatment tool according to claim 10, wherein the second sliding portion has a piston that is provided at one end part of the wire holding part, a cylinder that movably accommodates the piston in an axial direction of the piston, and a ring-shaped elastic member that is provided on an outer periphery of the piston and that is in contact with an inner wall surface of the cylinder.

13. The endoscope treatment tool according to claim 12, wherein the ring-shaped elastic member is an O-ring.

14. An endoscope device comprising:

a first treatment tool that is the endoscope treatment tool according to claim 10;

a second treatment tool; and an endoscope that has a first treatment tool channel into which the first treatment tool is insertable and a second treatment tool channel into which the second treatment tool is insertable.

15. A treatment method comprising:

by using the endoscope device according to claim 14, disposing the distal end part of the first treatment tool at a lesion part in a body through the first treatment tool channel of the endoscope;

gripping the lesion part with the grip part of the first treatment tool;

lifting, in a state where the lesion part is gripped, the lesion part by bending the bendable part of the first treatment tool; and treating, in a state where the lesion part is lifted, a lower part of the lesion part with the second treatment tool inserted into the second treatment tool channel of the endoscope.

* * * * *